United States Patent
He et al.

(10) Patent No.: US 9,797,004 B2
(45) Date of Patent: Oct. 24, 2017

(54) METHODS AND COMPOSITIONS FOR DETERMINATION OF VECTOR BACKBONE IN A NUCLEIC ACID SAMPLE

(71) Applicant: Syngenta Participations AG, Basel (CH)

(72) Inventors: Chengkun He, Research Triangle Park, NC (US); Chunyang Fan, Research Triangle Park, NC (US); John Ke, Research Triangle Park, NC (US); Heng Zhong, Research Triangle Park, NC (US); Doug Russell, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 531 days.

(21) Appl. No.: 13/913,937

(22) Filed: Jun. 10, 2013

(65) Prior Publication Data
US 2013/0330733 A1 Dec. 12, 2013

Related U.S. Application Data

(60) Provisional application No. 61/658,802, filed on Jun. 12, 2012.

(51) Int. Cl.
*C12Q 1/68* (2006.01)
*C12N 15/82* (2006.01)

(52) U.S. Cl.
CPC ....... *C12Q 1/6848* (2013.01); *C12N 15/8201* (2013.01); *C12N 15/8207* (2013.01); *C12N 15/8209* (2013.01); *C12Q 1/6806* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 6,137,033 A | 10/2000 | Estruch et al. | |
| 6,291,156 B1 | 9/2001 | Estruch et al. | |
| 6,429,360 B1 | 8/2002 | Estruch et al. | |
| 6,451,563 B1 * | 9/2002 | Wittig | C12N 15/10 435/194 |
| 6,846,970 B1 | 1/2005 | Christou et al. | |
| 7,098,031 B2 | 8/2006 | Choulika et al. | |
| 7,741,533 B2 | 6/2010 | Jung et al. | |
| 7,763,775 B2 | 7/2010 | Puthigae et al. | |
| 7,847,154 B2 | 12/2010 | Puthigae et al. | |
| 7,858,766 B2 | 12/2010 | Pitcovski et al. | |
| 7,880,057 B2 | 2/2011 | Rommens et al. | |
| 7,947,868 B2 | 5/2011 | Rommens et al. | |
| 7,951,995 B2 | 5/2011 | Guida, Jr. et al. | |
| 7,968,770 B2 | 6/2011 | Guida, Jr. et al. | |
| 2008/0108072 A1 | 5/2008 | Chicoine et al. | |
| 2008/0134361 A1 | 6/2008 | Jung | |
| 2009/0328253 A1 | 12/2009 | Gilbertson et al. | |
| 2010/0146662 A1 | 6/2010 | de Vetten et al. | |
| 2010/0240059 A1 | 9/2010 | Chicoine et al. | |
| 2011/0015084 A1 | 1/2011 | Christian et al. | |
| 2011/0138504 A1 | 6/2011 | Beazley et al. | |
| 2011/0162098 A1 | 6/2011 | Mason et al. | |
| 2011/0162112 A1 | 6/2011 | Li et al. | |

FOREIGN PATENT DOCUMENTS

WO    WO 2012/051199 A2    4/2012

OTHER PUBLICATIONS

Delenda et al. (Gene Therapy, 2005, 12:S36-S50).*
Shou et al. (Molecular Breeding, 2004, 13:201-208).*
Hernandez et al. (Transgenic Research, 2003, vol. 12, p. 201-208).*
Agrawal et al. "Clean DNA transformation: co-integration and expression analysis of five minimal transgene cassettes in rice" *Advances in Rice Genetics, supplement to Rice Genetics IV. Proceedings of the Fourth International Rice Genetics Symposium,* Oct. 22-27, 2000, Los Banos, Philippines, 536-538.
Agrawal et al. "Transformation of plants with multiple cassettes generates simple transgene integration patterns and high expression levels", *Molecular Breeding*, 2005, 16:247-260.
Beyene et al. "Unprecedented enhancement of transient gene expression from minimal cassettes suing a double terminator", *Plant Cell Rep.*, 2011, 30: 13-25.
Fu et al. "Linear transgene constructs lacking vector backbone sequences generate low-copy-number transgenic plants with simple integration patterns", *Transgenic Research*, 9:11019, 2000.
Gadaleta et al. "A transgenic durum wheat line that is free of marker genes and expresses *1Dy10*", *Journal of Cereal Science*, 48, 2008, 439-445.
International Search Report and Written Opinion Corresponding to International Application No. PCT/US2013/044920; dated Nov. 22, 2013; 13 Pages.
Kohli et al. "Transgene integration, organization and interaction in plants", *Plant Molecular Biology*, 52:247-258, 2003.
Shou et al. "Assessment of transgenic maize events produced by particle bombardment or Agrobacterium-mediated transformation", *Molecular Breeding*, 13:201-208, 2004.
Taverniers et al. "Event-Specific Plasmid Standards and Real-Time PCR Methods for Transgenic Bt11, Bt176, and GA21 Maize and Transgenic GT73 Canola", *J. Agric. Food Chem.*, 2005, 53, 3041-3052.
Yang et al. "Event Specific Qualitative and Quantitative Polymerase Chain reaction Detection of Genetically Modified MON863 Maize Based on the 5'-Transgene Integration Sequence", *J. Agric. Food Chem.*, 2005, 53, 9312-9318.
Zarka et al. "Insertion and Characterization of the *cry1Ia1* Gene in the Potato cultivar Spunta for Resistance to Potato Tuber Moth", *J. Amer. Soc. Hort. Sci.* 135(4):317-324, 2010.

* cited by examiner

*Primary Examiner* — Stephanie K Mummert
(74) *Attorney, Agent, or Firm* — Yoshimi D. Barron

(57) ABSTRACT

The invention provides methods and compositions for detecting and/or quantifying vector backbone in a nucleic acid preparation comprising a polynucleotide of interest using amplification assays that amplify a junction located between the polynucleotide of interest and the vector backbone, under conditions whereby amplification can occur, wherein the junction comprises a recognition site for a nuclease, and detecting the absence of an amplification product, whereby the absence of the amplification product indicates low or no vector backbone and/or quantifying the amount of amplification product to determine the amount of vector backbone in the nucleic acid preparation.

9 Claims, 4 Drawing Sheets

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial
<220> FEATURE:
<223> OTHER INFORMATION: RT-PCR primer sequence

<400> SEQUENCE: 1
catggaagcc atcacaaacg                                                20

<210> SEQ ID NO 2
<211> LENGTH: 21
<212> TYPE: DNA
<213> ORGANISM: Artificial
<220> FEATURE:
<223> OTHER INFORMATION: RT-PCR primer sequence

<400> SEQUENCE: 2
ttatacgcaa ggcgacaagg t                                              21

<210> SEQ ID NO 3
<211> LENGTH: 24
<212> TYPE: DNA
<213> ORGANISM: Artificial
<220> FEATURE:
<223> OTHER INFORMATION: RT-PCR probe sequence

<400> SEQUENCE: 3
catgatgaac ctgaatcgcc agcg                                           24

<210> SEQ ID NO 4
<211> LENGTH: 20
<212> TYPE: DNA
<213> ORGANISM: Artificial
<220> FEATURE:
<223> OTHER INFORMATION: RT-PCR primer sequence

<400> SEQUENCE: 4
gtggacagcc tggacgagat                                                20

<210> SEQ ID NO 5
<211> LENGTH: 19
```

```
<212> TYPE: DNA
<213> ORGANISM: Artificial
<220> FEATURE:
<223> OTHER INFORMATION: RT-PCR primer sequence

<400> SEQUENCE: 5
gaagccactg cggaacatg                                                  19

<210> SEQ ID NO 6
<211> LENGTH: 26
<212> TYPE: DNA
<213> ORGANISM: Artificial
<220> FEATURE:
<223> OTHER INFORMATION: RT-PCR probe sequence

<400> SEQUENCE: 6
cagaacaaca acgtgccacc tcgaca                                          26

<210> SEQ ID NO 7
<211> LENGTH: 337
<212> TYPE: DNA
<213> ORGANISM: Artificial
<220> FEATURE:
<223> OTHER INFORMATION: Backbone junction sequence

<400> SEQUENCE: 7
agtgagctga taccgctcgc cgcagccgaa cgaccgagcg cagcgagtca gtgagcgagg      60
agttagaaga gcttaagcgg ccgcggcgcg ccgcccaatg ccaagctttt tcacaccgca     120
tatggtgcac tctcagtaca atctgctctg atgccgcata gttaagccag ccccgacacc     180
cgccaacacc cgctgacgcg ccctgacggg cttgtctgct cccggcatcc gcttacagac     240
aagctgtgac cgtctccggg agctgcatgt gtcagaggtt ttcaccgtca tcaccgaaac     300
gcgcgagacg aaaggggacc ccggacccaa gcttgca                              337

<210> SEQ ID NO 8
<211> LENGTH: 317
<212> TYPE: DNA
<213> ORGANISM: Artificial
<220> FEATURE:
<223> OTHER INFORMATION: Backbone junction sequence

<400> SEQUENCE: 8
gtgagctgat accgctcgcc gcagccgaac gaccgagcgc agcgagtcag tgagcgagga      60
gttagaagag cttaagcggc cgcggcgcgc cgcccaatgc caagcttttt cacaccgcat     120
atggtgcact ctcagtacaa tctgctctga tgccgcatag ttaagccagc ccgacaccc     180 gccaacaccc gctgacgcgc cctgacgggc ttgtctgctc ccggcatccg cttacagaca     240
agctgtgacc gtctccggga gctgcatgtg tcagaggttt tcaccgtcat caccgaaacg     300
cgcgagacga aagggga                                                   317

<210> SEQ ID NO 9
<211> LENGTH: 333
<212> TYPE: DNA
<213> ORGANISM: Artificial
<220> FEATURE:
<223> OTHER INFORMATION: Backbone junction sequence

<400> SEQUENCE: 9
agctgatacc gctcgccgca gccgaacgac cgagcgcagc gagtcagtga gcgaggagtt      60
agaagagctt aagcggccgc ggcgcgccgc ccaatgccaa gcttttcac accgcatatg     120
```

```
gtgcactctc agtacaatct gctctgatgc cgcatagtta agccagcccc gacacccgcc      180
aacacccgct gacgcgccct gacgggcttg tctgctcccg gcatccgctt acagacaagc      240
tgtgaccgtc tccgggagct gcatgtgtca gaggttttca ccgtcatcac cgaaacgcgc      300
gagacgaaag gggaccccgg acccaagctt gca                                   333
```

```
<210> SEQ ID NO 10
<211> LENGTH: 24
<212> TYPE: DNA
<213> ORGANISM: Artificial
<220> FEATURE:
<223> OTHER INFORMATION: RT-PCR primer sequence

<400> SEQUENCE: 10
gcgaggagtt agaagagctt aagc                                              24

<210> SEQ ID NO 11
<211> LENGTH: 25
<212> TYPE: DNA
<213> ORGANISM: Artificial
<220> FEATURE:
<223> OTHER INFORMATION: RT-PCR primer sequence

<400> SEQUENCE: 11
attgtactga gagtgcacca tatgc                                             25

<210> SEQ ID NO 12
<211> LENGTH: 23
<212> TYPE: DNA
<213> ORGANISM: Artificial
<220> FEATURE:
<223> OTHER INFORMATION: RT-PCR probe sequence

<400> SEQUENCE: 12
ccgcccaatg ccaagctttt tca                                               23

<210> SEQ ID NO 13
<211> LENGTH: 14
<212> TYPE: DNA
<213> ORGANISM: Artificial
<220> FEATURE:
<223> OTHER INFORMATION: RT-PCR primer sequence

<400> SEQUENCE: 13
tgcggcggct gcat                                                         14

<210> SEQ ID NO 14
<211> LENGTH: 19
<212> TYPE: DNA
<213> ORGANISM: Artificial
<220> FEATURE:
<223> OTHER INFORMATION: RT-PCR preimer sequence

<400> SEQUENCE: 14
gtttcgcttg gtggtcgaa                                                    19

<210> SEQ ID NO 15
<211> LENGTH: 22
<212> TYPE: DNA
<213> ORGANISM: Artificial
<220> FEATURE:
<223> OTHER INFORMATION: RT-PCR probe sequence

<400> SEQUENCE: 15
cgcttgatcc ggctacctgc cc                                                22
```

```
<210> SEQ ID NO 16
<211> LENGTH: 324
<212> TYPE: DNA
<213> ORGANISM: Artificial
<220> FEATURE:
<223> OTHER INFORMATION: Backbone junction sequence

<400> SEQUENCE: 16
gctgataccg ctcgccgcag ccgaacgacc gagcgcagcg agtcagtgag cgaggagtta      60
gaagagctta aagttacgct agggataaca gggtaatata ggcggccgcg gcgcgccgcc     120
caatcccaag cttaagcttt ttcacaccgc aattggtgca ctctcagtac aatctgctct     180
gaagccgctt agttaagcca gccccgacac ccgccaacac ccgctgacgc gccctgacgg     240
gcttgtctgc tcccggcaac cgcttacaga caagctgtga ccgtctccgg gagctggatc     300
tgtcagaggt tttcaccgtc aaca                                            324

<210> SEQ ID NO 17
<211> LENGTH: 26
<212> TYPE: DNA
<213> ORGANISM: Artificial
<220> FEATURE:
<223> OTHER INFORMATION: RT-PCR preimer sequence

<400> SEQUENCE: 17
gaagagctta aagttacgct agggat                                          26

<210> SEQ ID NO 18
<211> LENGTH: 24
<212> TYPE: DNA
<213> ORGANISM: Artificial
<220> FEATURE:
<223> OTHER INFORMATION: RT-PCR primer sequence

<400> SEQUENCE: 18
gtgaaaaagc ttaagcttgg gatt                                            24

<210> SEQ ID NO 19
<211> LENGTH: 24
<212> TYPE: DNA
<213> ORGANISM: Artificial
<220> FEATURE:
<223> OTHER INFORMATION: RT-PCR probe sequence

<400> SEQUENCE: 19
acagggtaat ataggcggcc gcgg                                            24

<210> SEQ ID NO 20
<211> LENGTH: 18
<212> TYPE: DNA
<213> ORGANISM: Artificial
<220> FEATURE:
<223> OTHER INFORMATION: RT-PCR primer sequence

<400> SEQUENCE: 20
accgccttcc tgatgctg                                                   18

<210> SEQ ID NO 21
<211> LENGTH: 20
<212> TYPE: DNA
<213> ORGANISM: Artificial
<220> FEATURE:
<223> OTHER INFORMATION: RT-PCR primer sequence
```

```
<400> SEQUENCE: 21
caccggcttc ttggtcttgt                                               20

<210> SEQ ID NO 22
<211> LENGTH: 26
<212> TYPE: DNA
<213> ORGANISM: Artificial
<220> FEATURE:
<223> OTHER INFORMATION: RT-PCR probe sequence

<400> SEQUENCE: 22
aactaccgct gccagttcca caccag                                        26
```

METHODS AND COMPOSITIONS FOR DETERMINATION OF VECTOR BACKBONE IN A NUCLEIC ACID SAMPLE

STATEMENT OF PRIORITY

This application claims the benefit, under 35 U.S.C. §119 (e), of U.S. Provisional Application No. 61/658,802 was filed on Jun. 12, 2012, the entire contents of which is incorporated by reference herein.

STATEMENT REGARDING ELECTRONIC FILING OF A SEQUENCE LISTING

A Sequence Listing in ASCII text format, submitted under 37 C.F.R. §1.821, entitled 9207-66TS_ST25.txt, 6,017 bytes in size, generated on May 31, 2013 and filed via EFS-Web, is provided in lieu of a paper copy. This Sequence Listing is hereby incorporated herein by reference into the specification for its disclosures.

FIELD OF THE INVENTION

The present invention relates to methods of detecting and/or quantifying vector backbone in nucleic acid preparations.

BACKGROUND OF THE INVENTION

Since the introduction of genetically modified (GM) crops, there has been a rapid adoption of the technology. The International Service for the Acquisition of Agri-Biotech Application (ISAAA) reported that the global acreage of GM crops reached a record 160 million hectares in 29 countries in 2011. United States of America, Brazil, Argentina, India, Canada and China represent the six largest countries for planting GM crops. Currently, the major GM field crops are soybean, corn, cotton and canola. Minor GM crops include papaya, sugarbeet, squash, potato and alfalfa. Foreign gene expression cassettes are typically delivered into plants by *Agrobacterium*-mediated transformation and biolistic bombardment transformation. *Agrobacterium tumefaciens* has been widely used for introducing genes into plants for purposes of basic research as well as for the generation of commercial transgenic crops. *Agrobacterium*-mediated transformation of plants can result in DNA sequences outside the T-DNA region, such as vector backbone, to integrate into the plant genome (Kononov et al. *Plant J* 11: 945-957 (1997); Wenck et al. *Plant Mol Biol* 34: 913-922 (1997); Shou et al. *Mol Breed* 13: 201-208 (2004)). It is common practice for vector backbone sequences to be removed before transforming foreign DNA into commercial crops using the particle bombardment transformation approach. Further, it has been reported that biolistic delivery of a linear construct with no vector backbone has been shown to produce a high percentage of events with intact single copy insertions (Fu et al. *Transgenic Res.* 9:11-19 (2000)).

The current approach to removing unwanted vector backbone sequences, i.e., the bacterial replication DNA region, prior to plant transformation involves restriction enzyme digestion, preparative gel electrophoresis, then confirmation by analytical gel electrophoresis against reference standards. However, the current approach has disadvantages: each construct must be checked for available sites for *E. coli* plasmid backbone removal for every construct. To estimate *E. coli* DNA in the preps, the DNA preparations need to be serially diluted and the diluted DNAs back transformed into *E. coli* to check for unwanted circular DNA. A calculation using this method is not accurate. Further, the process is inefficient and a large amount of the DNA intended for transformation is wasted. Thus, this method is complicated, time consuming, has low throughput and is inaccurate. Additionally, no assay is available for detection of *E. coli* backbone containing plasmid DNA elements such as ColE region because (1) Taq DNA polymerase used in the detection assays is contaminated with *E. coli* DNA and/or TAQ expression plasmid DNA each providing a potential source of plasmid DNA elements such as ColE region which interferes with measurement of ColE in the DNA sample intend for use in transformation.

The present invention overcomes the shortcomings in the art by providing methods for determining the presence of vector backbone in purified nucleic acid preparations that are not only rapid but have greater accuracy.

SUMMARY OF THE INVENTION

Accordingly, in one aspect, the invention provides a method of detecting vector backbone in a nucleic acid preparation, the nucleic acid preparation comprising a polynucleotide of interest (POI), the method comprising: performing an amplification reaction to amplify a junction located between the POI and a vector backbone, under conditions whereby amplification can occur, wherein the junction comprises a recognition site for a nuclease; and detecting the absence of an amplification product, whereby the absence of the amplification product indicates low or no vector backbone in said nucleic acid preparation. In some aspects of the invention, the junction of the vector comprises said recognition site linked at one end to a synthetic polynucleotide (SN) and the junction is linked at one end to the POI via the SN, and the amplification product comprises the recognition site and at least a portion of the SN. In additional aspects of the invention, the junction of the vector comprises said recognition site linked at one end to a synthetic polynucleotide SN1 and linked at the other end to a synthetic polynucleotide SN2 and the SN1 of the junction is linked to one of the vector backbone or the POI and the SN2 of the junction is linked to the other of the vector backbone or the POI.

A further aspect of the present invention provides a method of selecting a nucleic acid preparation of a polynucleotide of interest (POI) having low or no vector backbone, the method comprising: performing an amplification assay to amplify a junction located between the POI and a vector backbone in one or more nucleic acid preparations, under conditions whereby amplification can occur, to produce an amplification product, wherein the junction comprises a recognition site for a nuclease; detecting the amount of amplification product; and selecting a nucleic acid preparation having no or a low amount of the amplification product, thereby selecting a nucleic acid preparation having low or no vector backbone in said nucleic acid preparation.

The present invention further provides a method of quantifying the amount of vector backbone in a nucleic acid preparation of a polynucleotide of interest (POI), the method comprising: performing an amplification assay to amplify at least a portion of a junction located between the POI and the vector backbone using a quantitative amplification assay, under conditions whereby amplification can occur, to produce an amplification product, wherein the junction comprises a recognition site for a nuclease; and quantifying the amount of amplification product the amount of amplification product in a quantitative amplification assay; wherein the amount of amplification product indicates the amount of vector backbone in said nucleic acid preparation.

In some aspects, the present invention provides a method of quantifying the amount of vector backbone in a nucleic acid preparation comprising a polynucleotide of interest (POI), the method comprising: (a) providing a nucleic acid preparation comprising a POI, wherein the vector backbone is linked to the POI at the 5'-end by a first junction, J1, comprising a nuclease recognition site, RS1, and/or linked at the 3'-end to the POI by a second junction, J2, comprising a nuclease recognition site, RS2; (b) performing quantitative amplification assays on the vector backbone and the POI in a sample of the nucleic acid preparation and in a control sample, the control sample comprising the vector backbone and the polynucleotide sequence of interest that has not been contacted by the nuclease; (c) determining a cycle threshold ($C_T$) value for the vector backbone ($C_{T(BB)}$) and a $C_T$ value for the POI ($C_{T(POI)}$) in the sample of the nucleic acid preparation and in the control sample, wherein (i) determining $C_{T(BB)}$ comprises contacting the sample from the nucleic acid preparation and the control sample with a first primer, P1, that specifically hybridizes the first junction upstream of the nuclease recognition site, RS1, a second primer, P2, that specifically hybridizes to the first junction, J1, downstream of the nuclease recognition site, RS1, and a first probe, PR1, that specifically hybridizes to a region of the junction between where the first and the second primers specifically hybridize, wherein each of the first primer and the second primer is oriented such that under amplification conditions, the junction is amplified; and/or contacting the sample from the nucleic acid preparation and the control sample with a third primer, P3, that specifically hybridizes to the second junction, J2, upstream of the nuclease recognition site, RS2, a fourth primer, P4, that specifically hybridizes to the second junction downstream of the nuclease recognition site, RS2, and a second probe, PR2, that specifically hybridizes to a region of the junction between the regions where the third and fourth primers specifically hybridize, wherein each of the third primer and the fourth primer is oriented such that under amplification conditions, the junction is amplified; and wherein if the sample comprises vector backbone, hybridization of PR1 and/or PR2 is detected; and (ii) determining ($C_{T(POI)}$) comprises contacting the sample from the nucleic acid preparation and the control sample with a fifth primer, P5, a sixth primer, P6, and a labeled probe, PR3, each of which hybridizes specifically to the POI, wherein each of P5 and P6 is oriented such that under amplification conditions, at least a portion of the POI is amplified; and wherein if the sample comprises the POI, hybridization of PR3 is detected; (d) determining the percentage vector backbone in the nucleic acid preparation, comprising: (i) subtracting the $C_{T(POI)}$ determined for the nucleic acid preparation from the $C_{T(BB)}$ determined for the nucleic acid preparation to obtain $\Delta C_{T(BB\text{-}POI(Prep))}$; (ii) subtracting the $C_{T(POI)}$ determined for the control from the $C_{T(BB)}$ determined for the control to obtain $\Delta C_{T(BB\text{-}POI(control))}$; (iii) subtracting $\Delta C_{T(BB\text{-}POI(control))}$ from $\Delta C_{T(BB\text{-}POI(Prep))}$ to obtain the $\Delta\Delta C_{T(Prep\text{-}Control)}$; and (iv) calculating the percentage vector backbone in the nucleic acid preparation from the formula $(1\div(2^{[\Delta\Delta CT(Prep\text{-}Control)]})\times 100)$; thereby quantifying the amount of vector backbone in the nucleic acid preparation.

In a further aspect of the invention, a method of measuring the continuity of a polynucleotide is provided, the method comprising: designing amplification primers that hybridize one on either side of a junction; wherein the junction comprises a recognition site for a nuclease; contacting the junction with said nuclease; performing an amplification reaction across said junction; and detecting an amplification product resulting from said amplification reaction, wherein the absence of the amplification product indicates loss of polynucleotide continuity.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1:
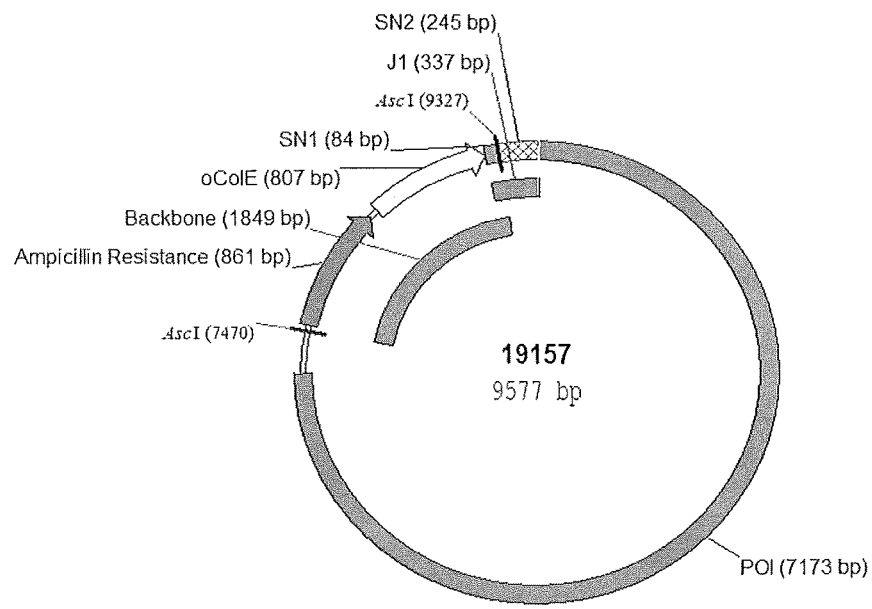
FIG. 1 shows a plasmid map of 19157.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

The present invention provides methods and compositions for detecting or quantifying the amount of vector backbone present in a nucleic acid preparation of a POI as well as methods for selecting a nucleic acid preparation of a POI having low or no vector backbone.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "heterologous" means foreign, exogenous, non-native and/or non-naturally occurring.

As used here, "homologous" means native. For example, a homologous nucleotide sequence or amino acid sequence is a nucleotide sequence or amino acid sequence naturally associated with a host cell into which it is introduced, a homologous promoter sequence is the promoter sequence that is naturally associated with a coding sequence, and the like. Thus, for example, a heterologous polynucleotide can be a polynucleotide that is heterologous (e.g., foreign or non-native) to the organism into which it is introduced and/or a heterologous polynucleotide can be a polynucleotide that is heterologous (e.g., foreign or non-native) to one or more nucleotide sequences to which it is linked (e.g., a promoter can be heterologous to a polynucleotide sequence to which it is operably linked).

"Polynucleotide of interest" or "nucleotide sequence of interest" or refers to any polynucleotide sequence which, when introduced into an organism, confers upon the organism a desired characteristic. Thus, for example, a polynucleotide of interest for introduction into a plant can include those that confer such characteristics as tolerance to abiotic stress, antibiotic resistance, virus resistance, insect resistance, disease resistance, or resistance to other pests, herbicide tolerance, improved nutritional value, improved performance in an industrial process, altered reproductive capability or the production of commercially valuable products such as enzymes or metabolites in the plant. In some embodiments, a "polynucleotide of interest" can encode a polypeptide and/or an inhibitory polynucleotide (e.g., a functional RNA).

A "functional" RNA includes any untranslated RNA that has a biological function in a cell, e.g., regulation of gene expression. Such functional RNAs include but are not limited to RNAi (e.g., siRNA, shRNA), miRNA, antisense RNA, ribozymes, RNA aptamers and the like.

By the term "express," "expressing" or "expression" (or other grammatical variants) of a nucleic acid coding sequence, it is meant that the sequence is transcribed. In particular embodiments, the terms "express," "expressing" or "expression" (or other grammatical variants) can refer to both transcription and translation to produce an encoded polypeptide.

"Wild-type" nucleotide sequence or amino acid sequence refers to a naturally occurring ("native") or endogenous nucleotide sequence (including a cDNA corresponding thereto) or amino acid sequence.

The terms "nucleic acid," "polynucleotide" and "nucleotide sequence" are used interchangeably herein unless the context indicates otherwise. These terms encompass both RNA and DNA, including cDNA, genomic DNA, partially or completely synthetic (e.g., chemically synthesized) RNA and DNA, and chimeras of RNA and DNA. The nucleic acid, polynucleotide or nucleotide sequence may be double-stranded or single-stranded, and further may be synthesized using nucleotide analogs or derivatives (e.g., inosine or phosphorothioate nucleotides). Such nucleotides can be used, for example, to prepare nucleic acids, polynucleotides and nucleotide sequences that have altered base-pairing abilities or increased resistance to nucleases. A nucleic acid, polynucleotide or nucleotide sequence can also be the complement (either a full complement or a partial complement) of a nucleic acid, polynucleotide or nucleotide sequence. Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage.

A "vector" is any nucleic acid molecule useful for the cloning of and/or transfer of a foreign nucleic acid into a cell. A vector consists of an origin of replication, multicloning sites, a selection marker and a POI. The origin of replication is a particular sequence in a genome at which replication is initiated. This can either involve the replication of DNA in living organisms such as prokaryotes and eukaryotes, or that of DNA or RNA in viruses, such as double-stranded RNA viruses. The four major types of vectors are plasmids, viral vectors, cosmids, and artificial chromosomes. The vector itself is generally a DNA sequence that consists of an insert (transgene) and a sequence that serves as the "backbone" of the vector. The purpose of a vector which transfers genetic information to another cell is typically to express the insert in the target cell. Vectors called expression vectors (expression constructs) can be used for the expression of the transgene in the target cell. A large number of vectors known in the art can be used to manipulate, deliver and express polynucleotides. Vectors can be engineered to contain sequences encoding selectable markers that provide for the selection of cells that contain the vector and/or have integrated some or all of the nucleic acid of the vector into the cellular genome. Such markers allow identification and/or selection of host cells that incorporate and express the proteins encoded by the marker. A "recombinant" vector refers to a vector that comprises one or more nucleotide sequences of interest (e.g., transgenes), e.g., one, two, three, four, five or more polynucleotide sequences of interest.

Non-viral vectors include, but are not limited to, plasmids, liposomes, electrically charged lipids (cytofectins), nucleic acid-protein complexes, and biopolymers. Viral vectors have been used in a wide variety of gene delivery applications in cells and whole organisms. Plant viral vectors that can be used include, but are not limited to, geminivirus vectors and/or tobomovirus vectors. In addition to a POI, a vector may also comprise one or more regulatory regions, and/or selectable markers useful in selecting, measuring, and monitoring nucleic acid transfer results (e.g., delivery to specific tissues, duration of expression, etc.).

In representative embodiments of this invention, the vector can be a plasmid vector.

As used herein, the term "polypeptide" encompasses both peptides and proteins (including fusion proteins), unless indicated otherwise.

"Introducing" in the context of a cell, tissue, and/or organism means contacting a nucleic acid molecule with the cell, tissue, and/or organism in such a manner that the nucleic acid molecule gains access to the interior of the cell, tissue, and/or organism. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into cells in a single transformation event, in separate transformation events or, for example, as part of a breeding protocol.

The term "transformation" as used herein refers to the introduction of a heterologous and/or isolated nucleic acid into a cell. Transformation of a cell may be stable or transient. Thus, for example, a transgenic plant cell, plant tissue, plant part and/or plant can be stably transformed or transiently transformed.

"Transient transformation" in the context of a polynucleotide means that a polynucleotide is introduced into the cell and does not integrate into the genome of the cell.

As used herein, "stably introducing," "stably introduced," "stable transformation" or "stably transformed" (and similar terms) in the context of a polynucleotide introduced into a cell, means that the introduced polynucleotide is stably integrated into the genome of the cell (e.g., into a chromosome or as a stable-extra-chromosomal element). As such, the integrated polynucleotide is capable of being inherited by progeny cells and organisms.

"Genome" as used herein includes the nuclear and/or plastid genome, and therefore includes integration of a polynucleotide into, for example, the chloroplast genome. Stable transformation as used herein can also refer to a polynucleotide that is maintained extrachromosomally, for example, as a minichromosome.

As used herein, the terms "transformed" and "transgenic" refer to any cell, tissue or organism that contains all or part of at least one recombinant or isolated nucleic acid, polynucleotide or nucleotide sequence. In representative embodiments, the recombinant or isolated nucleic acid, polynucleotide or nucleotide sequence is stably integrated into the genome of the organism (e.g., into a chromosome or as a stable extra-chromosomal element), so that it is passed on to subsequent generations of the cell or organism.

A nucleic acid preparation of a POI that can be selected for low or no vector backbone or a nucleic acid preparation of a POI for which the vector backbone can be detected or quantified using the methods of the present invention can be prepared from any suitable organism. Thus, exemplary organisms can include, but are not limited to, a plant, an insect, a mammal, a reptile, an amphibian, a bird, a nematode, a virus, a bacterium, an archaea, a mycoplasma, a fish, a fungus, a protozoan, a protist, and the like.

A nucleic acid preparation for use in transformation of an organism can be prepared by isolating the POI and introducing it into a vector for the purpose of increasing the quantity of the POI (i.e., replication or amplification in, for example, a plasmid vector). Following amplification, the vector can be contacted with one or more nucleases (e.g., restriction enzymes) that recognize and cut a nuclease recognition site (e.g., a restriction site) located between the vector backbone and the POI and which can then release the POI from the backbone of the vector. The preparation then contains free POI, free vector backbone and potentially both uncut vector and partially cut vector in which some of the POI is still linked on one end to the vector backbone. Preparative gel electrophoresis can be used to separate these different fractions but it is often difficult to determine the effectiveness of the separation techniques and to accurately determine the amount of vector backbone that remains in the nucleic acid preparation after the separation has been performed. Assays for detecting vector backbone that hybridize to and amplify only vector backbone sequences are not accurate due to the presence of *E. coli* in the commercial Taq DNA polymerase products as well as the possibility of the presence of *E. coli* sequences from the vector itself. Thus, a calculation for vector backbone in a nucleic acid preparation is not accurate when both primers hybridize to the vector backbone and may result in false vector backbone signal.

Therefore, to address this problem, the present invention provides methods and compositions for detecting and/or quantifying vector backbone in a nucleic acid preparation of a POI, as well as methods for selecting a nucleic acid preparation of a POI having low or no vector backbone. Once the nucleic acid preparations have been determined to have low or no vector backbone, they can be used for any purpose including directly for transformation. The methods of this invention are particularly useful for biolistic transformation where one desires an expression cassette for transforming an organism that simply comprises the POI(s) and any regulatory sequences desired but without any vector or other unwanted sequences.

Accordingly, in one embodiment, the present invention provides a method of detecting vector backbone in a nucleic acid preparation, the method comprising: performing an amplification reaction to amplify a junction located between the POI and the vector backbone, under conditions whereby amplification can occur, wherein the junction comprises a recognition site for a nuclease; and detecting the absence of an amplification product, whereby the absence of the amplification product indicates low or no vector backbone in the nucleic acid preparation. In some embodiments, detecting further comprises detecting the presence of an amplification product, whereby the presence of the amplification product indicates vector backbone in the nucleic acid preparation.

In further embodiments, the present invention provides a method of selecting a nucleic acid preparation of a POI having low or no vector backbone, the method comprising: performing an amplification reaction to amplify a junction of the vector located between the POI and the vector backbone in one or more nucleic acid preparations, under conditions whereby amplification can occur, to produce an amplification product, wherein the junction comprises a recognition site for a nuclease; detecting the amount of amplification product; and selecting a nucleic acid preparation having no or a low amount of the amplification product, thereby selecting a nucleic acid preparation having low or no vector backbone. In particular embodiments, selecting a nucleic acid preparation having low or no vector backbone comprises selecting a nucleic acid preparation that has an amount of vector backbone in the nucleic acid preparation of below about 0.5%. Thus, in some embodiments, selecting a nucleic acid preparation having low or no vector backbone comprises selecting a nucleic acid preparation that has an amount of vector backbone in the nucleic acid preparation of below about 0.5%, 4.75%, 4.5%, 4.25%, 4%, 3.75%, 3.5%, 3.25%, 3%, 2.75%, 2.5%, 2.25%, 2%, 1.9%, 1.8%, 1.7%, 1.6%, 1.5%, 1.4%, 1.2%, 1.1%, 1%, 0.95%, 0.9%, 0.85%, 0.8%, 0.75%, 0.7%, 0.65%, 0.6%, 0.55%, 0.5%, 0.49%, 0.48%, 0.47%, 0.46%, 0.45%, 0.44%, 0.43%, 0.42%, 0.41%, 0.4%, 0.39%, 0.38%, 0.37%, 0.36%, 0.35%, 0.34%, 0.33%, 0.32%, 0.31%, 0.3%, 0.29%, 0.28%, 0.27%, 0.26%, 0.25%, 0.24%, 0.23%, 0.22%, 0.21%, 0.2%, 0.19%, 0.18%, 0.17%, 0.16%, 0.15%, 0.14%, 0.13%, 0.12%, 0.11%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, or even less, and the like, and any range therein. Thus, in some particular embodiments, selecting a nucleic acid preparation having low or no vector backbone comprises selecting a nucleic acid preparation that has an amount of vector backbone in the nucleic acid preparation of less than about 0.5%, less than about 0.25%, less than about 0.1%, less than about 0.01%, or even less than about 0.001%.

In other embodiments of the present invention, a method is provided for quantifying the amount of vector backbone in a nucleic acid preparation of a POI, the method comprising: performing an amplification reaction to amplify at least a portion of a junction of the vector located between the POI and the plasmid vector backbone using a quantitative amplification assay, under conditions whereby amplification can occur, to produce an amplification product, wherein the junction comprises a recognition site for a nuclease; and quantifying the amount of amplification product; wherein the amount of amplification product indicates the amount of vector backbone in the nucleic acid preparation.

In still other embodiments, the present invention provides a method of detecting plasmid vector backbone in a nucleic acid preparation of a POI, wherein the plasmid vector backbone is an *E. coli*-based plasmid vector backbone, the method comprising: performing an amplification reaction to amplify a region of the plasmid vector backbone that does not comprise ColE, under conditions whereby amplification can occur; and detecting the presence or absence of an amplification product, whereby the presence of the amplification product indicates plasmid vector backbone in the nucleic acid preparation and the absence of the amplification product indicates low or no backbone in the nucleic acid preparation.

Other embodiments of the invention provide a method of quantifying the amount of plasmid vector backbone in a nucleic acid preparation of a POI, wherein the plasmid vector backbone is an *E. coli*-based plasmid vector backbone, the method comprising: performing an amplification reaction to amplify a region of the plasmid vector backbone that does not comprise ColE and/or an ampicillin resistant gene, under conditions whereby amplification can occur, to produce an amplification product; and quantifying the amount of amplification product, wherein the amount of amplification product indicates the amount of plasmid vector backbone in the nucleic acid preparation. Thus, in some embodiments of the invention, the *E. coli* backbone can be used in the amplification reactions for detecting or quantifying vector backbone according to this invention as long as the backbone does not comprise ColE and/or an ampicillin resistant gene. Accordingly, in some embodiments, the region of the *E. coli* vector backbone that does not comprise ColE and/or an ampicillin resistant gene and that is amplified is an *E. coli* polynucleotide. In other embodiments, the region of *E. coli* vector backbone that does not comprise ColE and/or an ampicillin resistant gene and that is amplified is a polynucleotide that is heterologous to *E. coli*. Thus, in some embodiments of this invention, the *E. coli* vector backbone can comprise polynucleotides that are heterologous to *E. coli*. Any suitable polynucleotide that is heterologous to *E. coli* can be used. Such heterologous polynucleotides include, but are not limited to, chloramphenicol acetyl transferase.

Additional embodiments of the invention provide a method of detecting plasmid vector backbone in a nucleic acid preparation of a POI, wherein the plasmid vector backbone is not an *E. coli*-based plasmid vector backbone, the method comprising: performing an amplification reaction to amplify a region of the plasmid vector backbone, under conditions whereby amplification can occur; and detecting the presence or absence of an amplification product, whereby the presence of the amplification product indicates plasmid vector backbone in the nucleic acid preparation and the absence of the amplification product indicates low or no backbone in the nucleic acid preparation.

In some embodiments, the present invention provides a method of quantifying the amount of plasmid vector backbone in a nucleic acid preparation of a POI that, wherein the plasmid vector backbone is not an *E. coli*-based plasmid vector backbone, the method comprising: performing an amplification reaction to amplify a region of the plasmid vector backbone, under conditions whereby amplification can occur, to produce an amplification product; and quantifying the amount of amplification product; wherein the amount of amplification product indicates the amount of plasmid vector backbone in the nucleic acid preparation.

In further embodiments, the present invention provides a method of quantifying the amount of vector backbone in a nucleic acid preparation comprising a POI, the method comprising: (a) providing a nucleic acid preparation comprising a POI, wherein the vector backbone is linked to the POI at the 5'-end by a first junction, J1, comprising a nuclease recognition site, RS1, and/or linked at the 3'-end to the POI by a second junction, J2, comprising a nuclease recognition site, RS2; (b) performing quantitative amplification assays on the vector backbone and the POI in a sample of the nucleic acid preparation and in a control sample, the control sample comprising the vector backbone and the POI that has not been contacted by the nuclease; (c) determining a cycle threshold ($C_T$) value for the vector backbone ($C_{T(BB)}$) and a $C_T$ value for the POI ($C_{T(POI)}$) in the sample of the nucleic acid preparation and in the control sample, wherein (i) determining $C_{T(BB)}$ comprises contacting the sample from the nucleic acid preparation and the control sample with a first primer, P1, that specifically hybridizes the first junction, J1, upstream of the nuclease recognition site, RS1, a second primer, P2, that specifically hybridizes to the first junction, J1, downstream of the nuclease recognition site, RS1, and a first probe, PR1, that specifically hybridizes to a region of the junction between the regions where the first and the second primers specifically hybridize, wherein each of the first primer and the second primer is oriented such that under amplification conditions, the junction is amplified; and/or contacting the sample from the nucleic acid preparation and control sample with a third primer, P3, that specifically hybridizes to the second junction, J2, upstream of the nuclease recognition site, RS2, a fourth primer, P4, that specifically hybridizes to the second junction downstream of the nuclease recognition site, RS2, and a second probe, PR2, that specifically hybridizes to a region of the junction between the regions where the third and fourth primers specifically hybridize, wherein each of the third primer and the fourth primer is oriented such that under amplification conditions, the junction is amplified; and wherein if the sample comprises vector backbone, hybridization of PR1 and/or PR2 is detected; and (ii) determining ($C_{T(POI)}$) comprises contacting the sample from the nucleic acid preparation and the control sample with a fifth primer, P5, a sixth primer, P6, and a labeled probe, PR3, each of which hybridizes specifically to the POI, wherein each of P5 and P6 is oriented such that under amplification conditions, at least a portion of the POI is amplified; and wherein if the sample comprises the POI, hybridization of PR3 is detected; (d) determining the percentage vector backbone in the nucleic acid preparation, comprising: (i) subtracting the $C_{T(POI)}$ determined for the nucleic acid preparation from the $C_{T(BB)}$ determined for the nucleic acid preparation to obtain $\Delta C_{T(BB-POI(Prep))}$; (ii) subtracting the $C_{T(POI)}$ determined for the control from the $C_{T(BB)}$ determined for the control to obtain $\Delta C_{T(BB-POI(control))}$; (iii) subtracting $\Delta C_{T(BB-POI(control))}$ from $\Delta C_{T(BB-POI(Prep))}$ to obtain the $\Delta \Delta C_{T(Prep-Control)}$; and (iv) calculating the percentage vector backbone in the nucleic acid preparation from the formula $(1 \div (2^{[\Delta\Delta CT(Prep-Control)]}) \times 100$; thereby quantifying the amount of vector backbone in the nucleic acid preparation.

In some embodiments of the invention, the first junction, J1, of the vector comprises the recognition site (RS1) linked at one end to a synthetic polynucleotide, SN1, and linked at the other end to a synthetic polynucleotide, SN2, and the SN1 of J1 is linked to one of the vector backbone or the POI and the SN2 of the J1 is linked to the other of the vector backbone or the POI and said second junction, J2, of the vector comprises said recognition site (RS2) linked at one end to a synthetic polynucleotide SN3 and linked at the other end to a synthetic polynucleotide SN4 and the SN3 of J2 is linked to one of the vector backbone or the POI and the SN4 of J2 is linked to the other of the vector backbone or the POI. Furthermore, as described herein, in some embodiments, SN1 and SN2 can be the same as each other or different from one another, SN3 and SN4 can be the same as each other or different from one another, and SN1 and SN2 can be different from SN3 and SN4. Thus, in some embodiments, the first primer, P1, can hybridize to the SN1 or the SN2, the second primer, P2, can hybridizes to the other of SN1 or SN2, the third primer, P3, can hybridize to the SN3 or the SN4, and the fourth primer, P4, can hybridize to the other of the SN3 or SN4.

In additional embodiments, the present invention provides a method of quantifying the amount of vector backbone in a nucleic acid preparation comprising a POI, the method comprising: (a) providing a nucleic acid preparation comprising a POI (POI), wherein the vector backbone is linked to the POI at the 5'-end by a first junction, J1, comprising a nuclease recognition site, RS1, and/or linked at-the 3'-end to the POI by a second junction, J2, comprising a nuclease recognition site, RS2; (b) performing quantitative amplification assays on the vector backbone and the POI in a sample of the nucleic acid preparation and in a control sample, the control sample comprising the vector backbone and the POI that has not been contacted by the nuclease; (c) determining a cycle threshold ($C_T$) value for the vector backbone ($C_{T(BB)}$) and a $C_T$ value for the POI ($C_{T(POI)}$) in the sample of the nucleic acid preparation and in the control sample, wherein (i) determining $C_{T(BB)}$ comprises contacting the sample from the nucleic acid preparation and the control sample with a first primer, P1, that specifically hybridizes the first junction, J1, upstream of the nuclease recognition site, RS1, a second primer, P2, that specifically hybridizes to the vector backbone downstream of the nuclease recognition site, RS1, and a first probe, PR1, that specifically hybridizes to a region between where the first and the second primers hybridize, wherein each of the first primer and the second primer is oriented such that under amplification conditions, the junction is amplified; and/or contacting the sample from the nucleic acid preparation and the control sample with a third primer, P3, that specifically hybridizes the vector backbone upstream of the nuclease recognition site, RS2, a fourth primer, P4, that hybridizes to J2 downstream of the nuclease recognition site, RS2, and a second probe, PR2, that specifically hybridizes to a region between where the third and fourth primers specifically hybridize, wherein each of the third primer and the fourth primer is oriented such that under amplification conditions, the junction is amplified; and wherein if the sample comprises vector backbone, hybridization of PR1 and/or PR2 is detected; and (ii) determining ($C_{T(POI)}$) comprises contacting the sample from the nucleic acid preparation and the control sample with a fifth primer, P5, a sixth primer, P6, and a labeled probe, PR3, each of which hybridizes specifically to the POI, wherein each of P5 and P6 is oriented such that under amplification conditions, the POI is amplified; and wherein if the sample comprises the POI, hybridization of PR3 is detected; (d) determining the percentage vector backbone in the nucleic acid preparation, comprising: (i) subtracting the $C_{T(POI)}$ determined for the nucleic acid preparation from the $C_{T(BB)}$ determined for the nucleic acid preparation to obtain $\Delta C_{T(BB-POI(Prep))}$; (ii) subtracting the $C_{T(POI)}$ determined for the control from the $C_{T(BB)}$ determined for the control to obtain $\Delta C_{T(BB-POI(control))}$; (iii) subtracting $\Delta C_{T(BB-POI(control))}$ from $\Delta C_{T(BB-POI(Prep))}$ to obtain the $\Delta \Delta C_{T(Prep-Control)}$; and (iv) calculating the percentage vector backbone in the nucleic acid preparation from the formula $(1 \div (2^{[\Delta\Delta CT(Prep-Control)]}) \times 100)$; thereby quantifying the amount of vector backbone in the nucleic acid preparation. Calculation of $C_T$ values is known in the art and can be carried out as described herein in Examples 1 and 2.

In some aspects of the invention, the POI of a nucleic acid preparation is previously contacted with a nuclease in order to cut/restrict the POI from the vector backbone and then the POI is separated from the vector backbone using, for example, gel electrophoresis resulting in a nucleic acid preparation comprising a POI that can be used with the methods of this invention.

In some embodiments of the invention, the first junction, J1, of the vector comprises said recognition site (RS1) linked at its 5'-end to a synthetic polynucleotide, SN1, and linked at its 3'-end to the vector backbone and the 5'-end of the SN1 of J1 can be linked to the 3'-end of the POI and/or the second junction, J2, of the vector comprises said recognition site (RS2) linked at the 3'-end to a synthetic polynucleotide SN2 and linked at the 5'-end to the vector backbone and the 3'-end of the SN2 of J2 can be linked to the POI.

In additional embodiments, a method of measuring the continuity of a polynucleotide is provided, the method comprising: designing amplification primers that hybridize one on either side of a junction; wherein the junction comprises a recognition site for a nuclease; contacting the junction with said nuclease; performing an amplification reaction across said junction; and detecting an amplification product resulting from said amplification reaction, wherein the absence of the amplification product indicates loss of polynucleotide continuity. In some embodiments the junction is located between a vector backbone and a POI. In other embodiments, the junction can comprise at least one synthetic polynucleotide linked to the nuclease recognition site. In still other embodiments, when the junction comprises one synthetic polynucleotide linked to the nuclease recognition site, the other side of the synthetic polynucleotide is linked to the vector backbone, and the amplification primers that hybridize one on either side of the junction hybridize to a portion of the synthetic polynucleotide and to a portion of the vector backbone. In still other embodiments of the invention, when the junction comprises two synthetic polynucleotides linked to either side of the nuclease recognition site, one of the synthetic polynucleotides (SN1) is linked to the vector backbone and the other synthetic polynucleotide (SN2) is linked to the POI and the amplification primers that hybridize one on either side of the junction hybridize to a portion of SN1 and to a portion of the SN 1.

As used herein, "continuity of a polynucleotide" means the nucleotides comprising the polynucleotide are intact and contiguous.

As used herein, "low" vector backbone means less than about 5% to about 0.001% or less vector backbone in a nucleic acid preparation of a POI. Thus, in some embodiments low vector backbone means less than about 5%, 4.75%, 4.5%, 4.25%, 4%, 3.75%, 3.5%, 3.25%, 3%, 2.75%, 2.5%, 2.25%, 2%, 1.9%, 1.8%, 1.7%, 1.6%, 1.5%, 1.4%, 1.2%, 1.1%, 1%, 0.95%, 0.9%, 0.85%, 0.8%, 0.75%, 0.7%, 0.65%, 0.6%, 0.55%, 0.5%, 0.49%, 0.48%, 0.47%, 0.46%, 0.45%, 0.44%, 0.43%, 0.42%, 0.41%, 0.4%, 0.39%, 0.38%, 0.37%, 0.36%, 0.35%, 0.34%, 0.33%, 0.32%, 0.31%, 0.3%, 0.29%, 0.28%, 0.27%, 0.26%, 0.25%, 0.24%, 0.23%, 0.22%, 0.21%, 0.2%, 0.19%, 0.18%, 0.17%, 0.16%, 0.15%, 0.14%, 0.13%, 0.12%, 0.11%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, or even less, and the like, and any range therein, of vector backbone in a nucleic acid preparation of a POI. Thus, in some particular embodiments, low vector backbone means less than about 0.5%, less than about 0.25%, less than about 0.1%, less than about 0.01%, or even less than about 0.001% detectable vector backbone in a nucleic acid preparation.

In some embodiments, the nucleic acid preparations comprising a POI that have been subjected to the methods of this invention and determined to have low or no vector backbone can then be used directly for transformation. In particular, a nucleic acid preparation comprising a polynucleotide(s) of interest that has been determined by the methods of this invention to have low or no vector backbone is useful for transformation of organisms via, for example, particle bombardment where it is often desirable to have a nucleic acid preparation of a polynucleotide(s) of interest that is free of unwanted nucleotide sequences such as those from a vector.

In some embodiments of the invention, the junction comprises a nuclease enzyme recognition site that is a recognition site for any suitable nuclease enzyme. Thus, in some embodiments, the nuclease recognition site is at least about 6 nucleotides. In other embodiments, the nuclease recognition site is at least about 6 nucleotides in length to about 40 nucleotides in length.

In some embodiments, the nuclease recognition site is a restriction endonuclease recognition site and the nuclease is a restriction endonuclease. In some embodiments, the restriction endonuclease can be any restriction nuclease useful with this invention that does not cut inside the POI. Accordingly, in some embodiments of the invention, the restriction endonuclease is a commercially available enzyme that includes, but is not limited to, any rare cutter, any 15-cutter, any 8-cutter, I-CeuI, PI-PspI, I-SceI, PI-SceI, I-PpoI, AscI, AsiSI, FseI, NotI, PacI, PmeI, SbfI, SfiI, SwaI, SgfI, SrfI, Sse8781I and/or SdaI.

In some embodiments, wherein there is more than one junction and therefore more than one recognition site, the recognition sites in the different junctions can be the same as one another or they can be different from one another (i.e., RS1=RS2 or RS1≠RS2).

In representative embodiments of the invention, the junction between the vector backbone and the polynucleotide sequence can comprise a nuclease recognition site and can further comprise one or two synthetic polynucleotides that flank the recognition site.

Thus, in some embodiments of the invention, the junction of the vector comprises a recognition site linked at one end to a synthetic polynucleotide (SN1). A junction of the vector that comprises a single synthetic polynucleotide (SN) can be linked at one end to the POI via the SN, and the amplification product can comprise the recognition site and at least a portion of the SN. Thus, in some particular embodiments, the junction of the vector can comprise a recognition site (RS) linked at the 3' end to the 5' end of a synthetic polynucleotide, SN, and at the 5' end to the 3' end of the vector backbone; the SN of the junction can be linked at the 3' end to the 5' end of the POI, the POI can be linked at the 5' end to the 3' end of the SN and at the 3' end to the 5' end of the vector backbone, and the vector backbone can be linked at the 5' end to the 3' end of the POI and at the 3' end to the 5' end of the RS. In other embodiments, the RS can be linked at the 5' end to the 3' end of the SN and at the 3' end to the 5' end of the vector backbone, the SN1 of the junction can be linked at the 5' end to the 3' end of the POI and at the 3' end to the 5' end of the RS, the POI can be linked at the 5' end to the 3' end of the vector backbone and at the 3' end to the 5' end of SN, and the vector backbone can be linked at the 5' end to the 3' end of the RS and at the 3' end to the 5' end of the POI.

In further embodiments of the invention, the junction of the vector can comprise a nuclease recognition site (RS) flanked at the 5' end and the 3' end with a synthetic polynucleotide (e.g., SN1, SN2). Thus, the junction can comprise a recognition site linked at one end to a synthetic polynucleotide, SN1, and linked at the other end to a synthetic polynucleotide, SN2, and the SN1 of the junction can be linked to one of the vector backbone or the POI and the SN2 of the junction can be linked to the other of the vector backbone or the POI.

Accordingly, in some particular embodiments, the junction of the vector comprises the recognition site (RS) linked at the 5' end to a synthetic polynucleotide, SN1; and the SN1 of the junction is linked at the 5' end to the 3' end of the vector backbone (VB) and the POI is linked to the 3' end to the 5' end of the vector backbone; or alternatively, the SN1 of the junction can linked at the 5' end to the 3' end of the POI and the POI can be linked at the 5' end to the 3' end of the vector backbone.

In further embodiments, when the junction comprises a restriction site flanked on either side by a synthetic polynucleotide, SN1 and SN2, the junction of the vector can comprise a recognition site (RS) linked at the 5' end to a synthetic polynucleotide, SN1, and linked at the 3' end to a synthetic polynucleotide, SN2; and the SN1 of the junction can be linked at the 5' end to the 3' end of the vector backbone (VB) and the SN2 of the junction can be linked at the 3' end to the 5' end of the POI and the POI can be linked at the 3' end to the 5' end of the VB. In further embodiments, a RS can be linked at the 5' end to the 3' end of SN1 and linked at the 3' end to the 5' end of SN2, the SN1 of the junction can be linked at the 5' end to the 3' end of the POI and the SN2 of the junction can be linked at the 3' end to the 5' end of the VB and the POI can be linked at the 5' end to the 3' end of the VB.

In some embodiments of the present invention, the junction comprises one or two synthetic polynucleotides flank the recognition site and the synthetic polynucleotides can be used for primer hybridization for amplifying across the junction. In other embodiments, when there is a single synthetic polynucleotide flanking the nuclease recognition site in the junction with the vector backbone flanking the other side of the recognition site, then the synthetic polynucleotide and the vector backbone can be used for primer binding and amplifying across the junction.

Thus, a synthetic polynucleotide can be any polynucleotide suitable for use with this invention (e.g., as a primer binding site). In some embodiments, the synthetic polynucleotide can be at least about 15 nucleotides in length. In other embodiments, the synthetic polynucleotide can be about 15 nucleotides to about 10,000 nucleotides (10 kb) or more. In other embodiments, the synthetic polynucleotide can be about 15 nucleotides to about 5000 nucleotides, about 15 nucleotides to about 2500 nucleotides, about 15 nucleotides to about 1000 nucleotides, about 15 nucleotides to about 500 nucleotides, and/or about 15 nucleotides to about 250 nucleotides. Thus, in some embodiments, the synthetic polynucleotide can be a length of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500, 10,000, 10,500, 11,000, or more nucleotides or any range therein.

In some embodiments, a synthetic polynucleotide of the invention is randomly generated. In additional embodiments, a synthetic polynucleotide does not share homology (e.g., does not hybridize under stringent conditions) with any *E. coli* nucleotide sequences. An example of stringent wash conditions is a 0.2×SSC wash at 65° C. for 15 minutes (for a description of SSC buffer, see, Sambrook et al. (2001) *Molecular Cloning: A Laboratory Manual*, 3rd ed. Cold Spring Harbor, N.Y.: Cold Spring Harbor Laboratory Press)). An example of highly stringent wash conditions is 0.15M NaCl at 72° C. for about 15 minutes.

In some particular embodiments, a vector comprising a POI can comprise two junctions each of which comprise a nuclease recognition site that can be flanked by one or two synthetic polynucleotides (e.g., RS1 flanked by SN1 and RS2 flanked by SN2; RS1 flanked by SN1 and SN2 and RS2 flanked by SN3 and SN4; RS1 flanked by SN1 and RS2 flanked by SN2 and SN3; RS1 flanked by SN1 and SN2 and RS2 flanked by SN3; and the like), wherein the junctions are each located between the POI and the vector backbone.

Thus, for example, in one embodiment, a first junction, J1, can comprise a recognition site (RS1) linked at one end to a synthetic polynucleotide, SN1, and linked at the other end to a synthetic polynucleotide, SN2, and the SN1 of J1 can be linked to one of the vector backbone or the POI and the SN2 of J1 can be linked to the other of the vector backbone or the POI, and a second junction, J2, of the vector can comprise a recognition site (RS2) linked at one end to a synthetic polynucleotide SN3 and linked at the other end to a synthetic polynucleotide SN4 and the SN3 of J2 can be linked to one of the vector backbone or the POI and the SN4 of J2 can be linked to the other of the vector backbone or the POI.

Accordingly, in particular embodiments, a first junction, J1, can comprise a recognition site (RS1) linked at the 5' end to the 3' end of a synthetic polynucleotide, SN1, and linked at the 3' end to the 5' end of a synthetic polynucleotide, SN2, and the SN1 of J1 can be linked at the 5' end to the 3' end of the POI and the SN2 of the J1 can be linked at the 3' end to the 5' end of the vector backbone, and a second junction, J2, of the vector can comprise a recognition site (RS2) linked at 5' end to the 3' end of a synthetic polynucleotide SN3 and linked at the 3' end to the 5' end of a synthetic polynucleotide SN4 and the SN3 of J2 can be linked at the 5' end to the 3' end of the vector backbone and the SN4 of J2 can be linked at the 3' end to the 5' end of the POI.

In additional embodiments of the invention, the vector can comprise two junctions each located between the vector backbone and the POI and the nuclease recognition site of each junction can be flanked by only one synthetic polynucleotide, the first junction, J1, of the vector can comprise a recognition site (RS1) linked at one end to a synthetic polynucleotide, SN1, and linked at the other end to the vector backbone and the other end of the SN1 of J1 can be linked to the POI and said second junction, J2, of the vector can comprise a recognition site (RS2) linked at one end to a synthetic polynucleotide SN2 and linked at the other end to the vector backbone and the other end of the SN2 of J2 can be linked to the POI.

Accordingly, in an exemplary embodiment, the first junction, J1, of the vector comprises said recognition site (RS1) linked at the 5' end to the 3' end of a synthetic polynucleotide, SN1, and linked at the 3' end to the 5' end of the vector backbone and the 5' end of the SN1 of J1 can be linked to the 3' end of the POI, and the second junction, J2, of the vector comprises a recognition site (RS2) linked at the 3' end to the 5' end of a synthetic polynucleotide SN2 and linked at the 5' end to the 3' end of the vector backbone and the 5' end of the SN2 of J2 is linked to the 3' end of the POI.

In some embodiments of the invention, the vector comprises a single junction between the vector backbone and the POI, which junction comprises a recognition site flanked on the 5' end and the 3' end by a synthetic polynucleotide, which can be the same or different from one another. Thus, for example, in some embodiments, the SN1 and SN2 that flank the same nuclease recognition site can be the same as each other. In other embodiments, the SN1 and SN2 can be different from one another. In other embodiments, when there are two junctions in a vector located between the vector backbone and the POI (e.g., two nuclease recognition sites, RS1, RS2), the synthetic polynucleotides flanking each nuclease recognition site can be the same or different from each other (e.g., when RS1 is flanked by SN1 and SN2 and RS2 is flanked by SN3 and SN4, SN1 and SN2 are different from SN3 and SN4 but SN1 and SN2 can be the same or different from one another and SN3 and SN4 can be the same or different from one another).

In representative embodiments, detecting the vector backbone and/or quantifying the amount of vector backbone in a nucleic acid preparation of a POI comprises performing an amplification reaction to amplify the junction between the POI and VB under conditions whereby amplification can occur.

In some embodiments, quantifying the amount of vector backbone in a nucleic acid preparation further comprises amplifying at least a portion of the POI and quantifying the amount of amplification product. In still other embodiments of the invention, quantifying the amount of vector backbone in a nucleic acid preparation further comprises amplifying at least a portion of a junction and/or at least a portion of the POI in a control (i.e., a vector that has not been contacted with the nuclease) and quantifying the amount of amplification product.

Methods for amplification of nucleic acids are well known in the art and include, for example, polymerase chain reaction (PCR) (see e.g., Saiki et al. *Science* 239:487-491 (1988)). PCR can be used to exponentially amplify small quantities of a target nucleotide sequence. A PCR reaction is performed in the presence of template sequence (the target nucleotide sequence), two oligonucleotide primers that are complementary to the target nucleotide sequence and which hybridize to opposite strands and flank the target nucleotide sequence, and a thermostable (e.g., taq) DNA polymerase. The reaction involves repeated heating and cooling cycles that result in template denaturation, primer annealing, and the extension of the annealed primers by DNA polymerase until sufficient copies of the target nucleotide sequence are generated.

Many variations of PCR are known such as hot start PCR, ligation-mediated PCR, mini-primer PCR, nested PCR, reverse transcription PCR and in silico PCR. A variation of PCR that is particularly useful with this invention is quantitative PCR (Q-PCR), which can be used to quantify a target nucleic acid with a high degree of precision. Quantitative PCR is commonly done in real-time (Quantitative Real-Time PRC) and uses fluorescent dyes that include but are not limited to Sybr Green, EvaGreen and/or fluorophore-containing nucleic acid probes (e.g., tetrachloro-6-carboxyfluorescein, TET), such as TaqMan, to measure the amount of amplified product in real time (See, e.g., Heid et al. *Genome Res.* 6:986-994 (1996); Ingham et al. *BioTechniques* 31 (1):132-140 (2001); Leutenegger, *Vet Sciences Tomorrow* 1:1-15 (2001)). TaqMan probes comprise a fluorophore linked to the 5'-end of the probe and a quencher linked to the 3'-end. Various fluorophores can be used including, but not limited to, 6-carboxyfluorescein (FAM), and/or tetrachlorofluorescein (TET). Quenchers useful with this invention include, but are not limited to, tetramethylrhodamine (TAMRA), and minor groove binders (MGB) that include but are not limited to dihydrocyclopyrroloindole tripeptide (DPI$_3$).

Accordingly, in some embodiments of the invention, quantifying the amount of amplification product comprises the use of a quantification assay. In some embodiments, the quantification assay is a quantitative amplification assay. In further embodiments, the quantitative amplification assay is a quantitative PCR assay. In particular embodiments, the quantitative PCR assay is a real time PCR assay.

Thus, in particular embodiments of this invention, wherein a single synthetic polynucleotide (SN) flanks the nuclease recognition site of the junction (between the POI and the recognition site), amplifying comprises hybridizing a first oligonucleotide primer to SN of the junction and hybridizing a second oligonucleotide primer to a portion of the vector backbone that flanks the recognition site of the junction and the amplification product comprises the recognition site, at least a portion of SN, and a portion of the vector backbone.

In other embodiments, wherein two synthetic polynucleotides (e.g., SN1, SN2) flank either side of the nuclease recognition site of the junction, the amplifying comprises hybridizing a first oligonucleotide primer to the SN1 of the junction and hybridizing a second oligonucleotide primer to the SN2 of the junction and the amplification product comprises the recognition site, at least a portion of SN1 and at least a portion of SN2.

In some embodiment of the present invention, an oligonucleotide primer can be about 10 to 50 nucleotides in length and a probe can be about 15 to about 40 nucleotides in length.

As described herein, a primer useful with this invention can be designed to hybridize to a synthetic polynucleotide or to a portion of the vector backbone that flanks the junction. In some embodiments, when a synthetic polynucleotide flank either side of the recognition site then the primers used for amplifying across the junction hybridize to each of the synthetic polynucleotides (e.g., P1 hybridizes to SN1 and P2 hybridizes to SN2). In other embodiments, when a synthetic polynucleotide flanks one side the recognition site and the vector backbone flanks the other side of the recognition site then the primers used for amplifying across the junction hybridize one to the synthetic polynucleotide and one to the vector backbone (e.g., P1 hybridizes to SN and P2 hybridizes to the vector backbone).

In additional embodiments of the invention, when the vector comprises two junctions between the POI and the vector backbone, the amplifying can comprise amplifying across both junctions by hybridizing oligonucleotide primers as described herein.

The amplification product (amplicon) can be of any suitable length for detecting the presence of the vector backbone. In some representative embodiments, the length of the amplification product is at least about 50 nucleotides in length. In other embodiments, the length of the amplification product is at least about 50 to about 200 nucleotides in length. In still other embodiments, the amplification product can be about 50 to about 150 nucleotides in length.

Thus, in representative embodiments, the amplicon can be a length of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 nucleotides or any range therein.

The conditions whereby amplification can occur are well known in the art as disclosed in, for example, Heid et al. *Genome Res.* 6:986-994 (1996); Ingham et al. *BioTechniques* 31 (1):132-140 (2001); Leutenegger, *Vet Sciences Tomorrow* 1:1-15 (2001).

In further embodiments of the invention, detecting the absence of an amplification product comprises detecting a labeled probe that is designed to hybridize to a portion of the target nucleotide sequence (e.g., amplification product that is generated as described herein). Thus, for example, when a probe labeled with a fluorophore and a quencher is utilized (e.g., TaqMan probe), a fluorescence signal is detected when the probe hybridizes to the target nucleotide sequence. In some embodiments, the absence of a fluorescence signal indicates the absence of the amplification product. Thus, in representative embodiments of this invention, the absence of a fluorescent signal from the labeled probe indicates low or no vector backbone in the nucleic acid preparation of the POI being tested.

In other embodiments of the invention, detecting the presence of an amplification product comprises detecting a labeled probe that is designed to hybridize to a portion of the target nucleotide sequence (i.e., amplification product that is generated as described herein). Thus, in some embodiments, the presence of a signal (e.g., a fluorescence signal) from a labeled probe indicates the presence of an amplification product. Therefore, in particular embodiments, the presence of a signal indicates the presence of plasmid vector backbone in a nucleic acid preparation of the POI being tested.

The present invention further provides compositions comprising plasmid vectors useful with the methods of the invention. Thus, in representative embodiments, the invention provides a recombinant plasmid vector, comprising a plasmid vector backbone linked to a POI by a first junction (J1) at the 5' end and a second junction (J2) at the 3' end, wherein J1, comprises in the following order (a) a first synthetic nucleotide sequence, SN1; (b) a first nuclease recognition site of at least 6 nucleotides in length, RS1; and (b) a second synthetic nucleotide sequence, SN2; and J2 comprises in the following order (a) a third synthetic nucleotide sequence, SN3; (b) a second restriction site of at least 6 nucleotides in length, RS2, and (b) a fourth synthetic nucleotide sequence, SN4.

In some embodiments, RS1 and RS2 are recognized by the same restriction endonuclease. In other embodiments of the invention, the nucleotide sequences of SN1, SN2, SN3 and/or SN4 are each 15 nucleotides to about 10,000 nucleotides (10 kb) or more nucleotides in length. In still other embodiments, one of SN1 or SN2 is zero nucleotides, and/or one of SN3 or SN4 is zero nucleotides (i.e., only one SN is present).

The present invention is more particularly described in the following examples that are intended as illustrative only since numerous modifications and variations therein will be apparent to those skilled in the art.

EXAMPLES

Example 1

Plasmid DNA Isolation, Purification and Quantification

Figure 2:
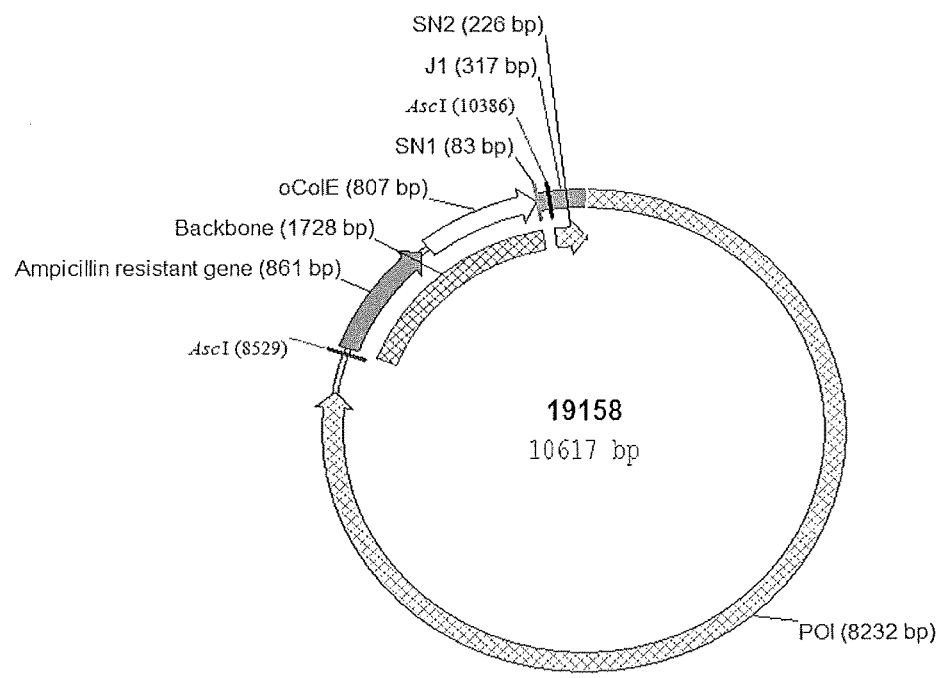
FIG. 2 shows a plasmid map of 19158.
Figure 3:
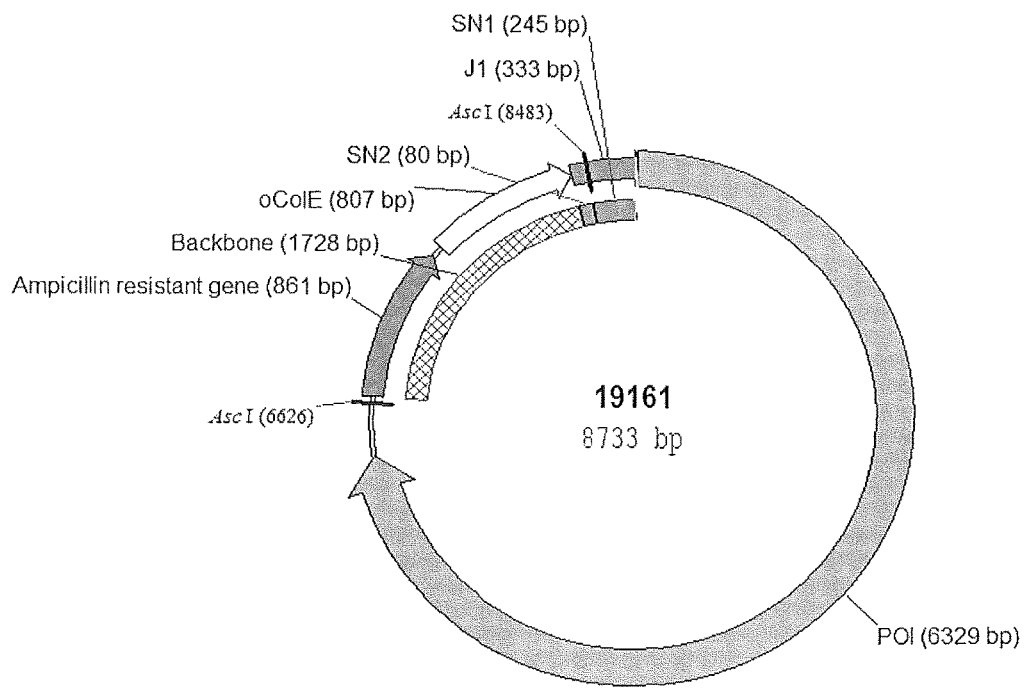
FIG. 3 shows a plasmid map of 19161.

Plasmid DNAs of 19157 (FIG. 1), 19158 (FIG. 2), 19161 (FIG. 3) and 19558 (FIG. 4) were isolated using GenElute™ HP plasmid midiprep kit (Sigma, St. Louis, Mo.). Plasmid DNA of 19975 (FIG. 5) was isolated by CsCl/ethidium bromide equilibrium centrifugation (Sambrook et al, (2001) *Molecular Cloning: A Laboratory Manual,* 3rd ed. Cold Spring Harbor, N.Y.: Cold Spring Harbor Laboratory Press) and low plasmid band was recovered. The concentrations of plasmid DNA samples were determined by fluorescence using Quant-iT™ PicoGreen® dsDNA Quantification Reagent Assay according to the manufacturer's protocol. All samples were measured in duplicate. If duplicates differed by >5%, the sample was re-measured.

The plasmid(s) are treated with a restriction nuclease enzyme to release (restrict or cut) the POI from the vector backbone. The resultant restricted nucleic acid preparation is further purified by gel purification techniques that are well known in the art, including preparative gel electrophoresis in order to separate any free vector backbone from the free POI. Finally, analytical gel electrophoresis gel electrophoresis is used for confirmation of the presence of the appropriate POI. At this stage, the nucleic acid preparation can be analyzed for the presence of remaining vector backbone using the methods of this invention.

Primers and Probes for Real-Time Quantitative PCR

Primers and probes were designed using Primer Express Software (V3.0) for Real-Time PCR (Applied Biosystems). For the bacterium backbone assays of 19157, 19158 and 19161, primers and probes were designed specifically to the region near and including the AscI recognition sites (RS) at J1 between the polynucleotide of interest (POI) fragment and backbone fragment (see the attached maps, FIGS. 1, 2 and 3, respectively). Thus, for example, the primers for J1 of 19157, 19158 and 19161 can be designed to hybridize to a portion of SN2 and a portion of SN1 and the resulting amplicon would include the AscI recognition site (RS) and a portion of SN1 and a portion of SN2.

Figure 5:
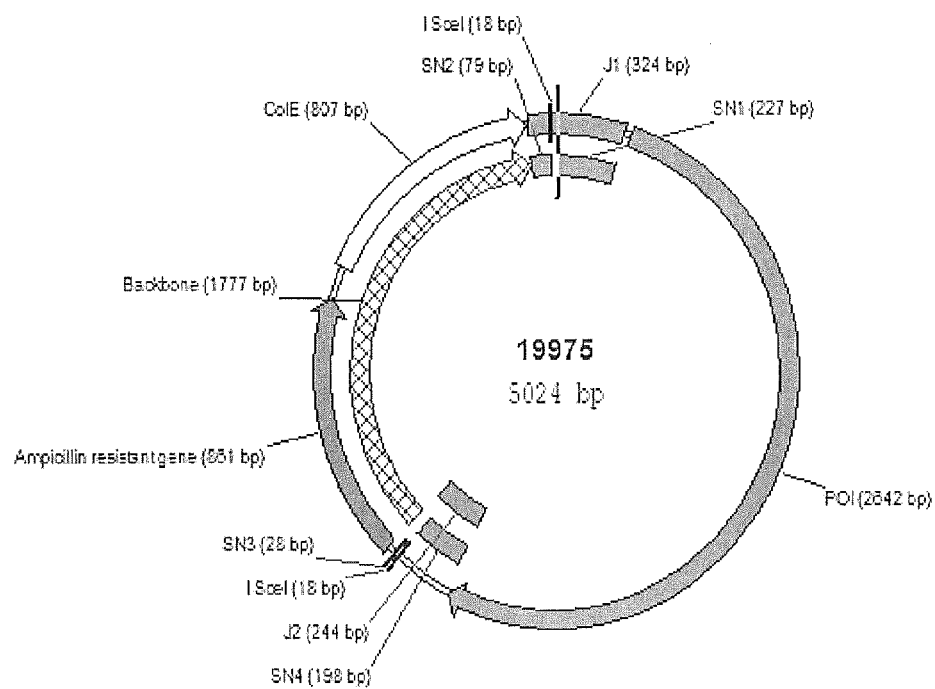
FIG. 5 shows a plasmid map of 19975.

For the bacterium backbone assays of 19975, primers and probes were designed specifically to one of the I SceI recognition sites (RS) between the polynucleotide-of-interest fragment and backbone fragment (see the attached map, FIG. 5). Thus, for example, the primers for J1 of 19975 can be designed to hybridize to a portion of SN2 and a portion of SN1 and the resulting amplicon would include the RS1 (ISceI) and a portion of SN1 and a portion of SN2. Alternatively or in addition, the primers for J2 of 19975 can be designed to hybridize to a portion of SN4 and a portion of SN3 and the resulting amplicon would include the RS2 (ISceI) and a portion of SN3 and a portion of SN4.

Figure 4:
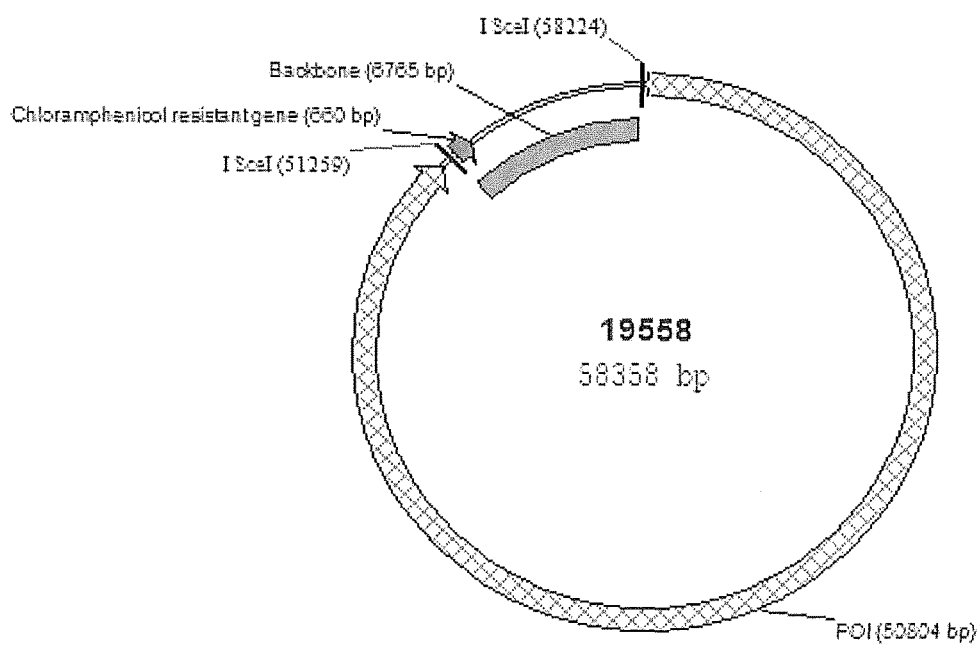
FIG. 4 shows a plasmid map of 19558.

For the backbone assay of 19558, primers and probes were designed to hybridize specifically to chloramphenicol resistance gene (Cat) (see the attached map, FIG. 4).

For the polynucleotide of interest (POI) assay for 19157, 19158 and 19161, primers and probes were for designed specifically to the kanamycin resistance gene. For the POI assay for 19558, primers and probes were for designed specifically to an insect resistance gene, Cry1AB. For the POI assay for 19975, primers and probes were designed specifically to a florescence protein gene, cAmCyan. All probes were labeled at their 5' end with a reporter fluorophore [tetrachloro-6-carboxyfluorescein (TET)] for the backbone assays (I SceI junction, AscI junction and chloramphenicol resistance gene (Cat)) and at the 3' end with a quenching dye (TAMRA (i.e., 6-carboxy-tetramethylrhodamine). For assaying the POI, the probe is labeled at the 5'-end with a fluorescent dye (FAM, 6-carboxyfluorescein) and at the 3' end with a quenching dye (TAMRA (i.e., 6-carboxy-tetramethylrhodamine).

Sequences:

(1) Construct ID: 19558
Backbone Assay, Targeting Chloramphenicol Resistance Gene (Assay ID: 1613). Assay Primer and Probe Sequences:

```
                                            (SEQ ID NO: 1)
Forward primer: 5'-CATGGAAGCCATCACAAACG-3'

(SEQ ID NO: 2)
Reverse primer: 5'-TTATACGCAAGGCGACAAGGT-3'

(SEQ ID NO: 3)
Probe: 5'-CATGATGAACCTGAATCGCCAGCG-3'
PCR amplicon: 74 bp
```

Polynucleotide of Interest (POI), Cry1Ab, Assay ID: 1118. Assay Primer and Probe Sequences:

```
                                            (SEQ ID NO: 4)
Forward primer: 5'-GTGGACAGCCTGGACGAGAT-3'

(SEQ ID NO: 5)
Reverse primer: 5'-GAAGCCACTGCGGAACATG-3'

(SEQ ID NO: 6)
Probe: 5'-CAGAACAACAACGTGCCACCTCGACA
PCR amplicon: 102 bp
```

(2) Construct IDs: 19157, 19158 and 19161
Backbone Junction Sequence (Between *E. Coli* Backbone Fragment and Polynucleotide-of-Interest POI; AscI Junction):

```
J1 sequence of 19157:
                                                              (SEQ ID NO: 7)
5'-agtgagctgataccgctcgccgcagccgaacgaccgagcgcagcgagtcagtgagcgaggagttagaagagcttaagcggc cgcggcgcgccgcccaatgccaagcttttcacaccgcatatggtgcactctcagtacaatctgctctgatgccgcatagttaagccag ccccgacacccgccaacacccgctgacgcgccctgacgggcttgtctgctcccggcatccgcttacagacaagctgtgaccgtctcc gggagctgcatgtgtcagaggttttcaccgtcatcaccgaaacgcgcgagacgaaaggggaccccggacccaagcttgca-3'
```

```
J1 sequence of 19158:
                                                              (SEQ ID NO: 8)
5'-gtgagctgataccgctcgccgcagccgaacgaccgagcgcagcgagtcagtgagcgaggagttagaagagcttaagcggcc gcggcgcgccgcccaatgccaagcttttcacaccgcatatggtgcactctcagtacaatctgctctgatgccgcatagttaagccagc cccgacacccgccaacacccgctgacgcgccctgacgggcttgtctgctcccggcatccgcttacagacaagctgtgaccgtctccg ggagctgcatgtgtcagaggttttcaccgtcatcaccgaaacgcgcgagacgaaagggga-3'
```

```
J1 sequence of 19161:
                                                              (SEQ ID NO: 9)
5'-agctgataccgctcgccgcagccgaacgaccgagcgcagcgagtcagtgagcgaggagttagaagagcttaagcggccgcg gcgcgccgcccaatgccaagcttttcacaccgcatatggtgcactctcagtacaatctgctctgatgccgcatagttaagccagcccc gacacccgccaacacccgctgacgcgccctgacgggcttgtctgctcccggcatccgcttacagacaagctgtgaccgtctccggga gctgcatgtgtcagaggttttcaccgtcatcaccgaaacgcgcgagacgaaaggggaccccggacccaagcttgca-3'
```

Backbone Assay Primers and Probe Sequences: (Assay ID: 1876)

Forward primer: 5'-GCGAGGAGTTAGAAGAGCTTAAGC-3' (SEQ ID NO: 10)

Reverse primer: 5'-ATTGTACTGAGAGTGCACCATATGC-3' (SEQ ID NO: 11)

Probe: 5'-CCGCCCAATGCCAAGCTTTTTCA-3' (SEQ ID NO: 12)
PCR amplicon: 88 bp

Polynucleotide of Interest, POI, Npt2, Assay Primer and Probe Sequences (Assay ID: 1072):

Forward primer: 5'-TGCGGCGGCTGCAT-3' (SEQ ID NO: 13)

Reverse primer: 5'-GTTTCGCTTGGTGGTCGAA-3' (SEQ ID NO: 14)

Probe: 5'-CGCTTGATCCGGCTACCTGCCC-3' (SEQ ID NO: 15)
PCR amplicon: 57 bp (3) Construct ID: 19975
Backbone Junction Sequence (Between *E. Coli* Backbone Fragment and Polynucleotide-of-Interest POI):

J1 sequence of 19975:

(SEQ ID NO: 16)

5'-gctgataccgctcgccgcagccgaacgaccgagcgcagcgagtcagtgagcgaggagttagaagagcttaaagttacgctag ggataacagggtaatataggcggccgcggcgcgccgcccaatcccaagcttaagcttttcacaccgcaattggtgcactctcagtac aatctgctctgaagccgcttagttaagccagccccgacaccgccaacaccgctgacgcgccctgacgggcttgtctgctcccggc aaccgcttacagacaagctgtgaccgtctccgggagctggatctgtcagaggttttcaccgtcaaca-3'

Backbone Assay Primers and Probe Sequences:

Forward primer: 5'-GAAGAGCTTAAAGTTACGCTAGGGAT-3' (SEQ ID NO: 17)

Reverse primer: 5'-GTGAAAAAGCTTAAGCTTGGGATT-3' (SEQ ID NO: 18)

Probe: 5'-ACAGGGTAATATAGGCGGCCGCGG-3' (SEQ ID NO: 19)
PCR amplicon: 85 bp

Polynucleotide of Interest (POI) cDMTAmCyan-01 Assay Primer and Probe Sequences:

Forward primer: 5'-ACCGCCTTCCTGATGCTG-3' (SEQ ID NO: 20)

Reverse primer: 5'-CACCGGCTTCTTGGTCTTGT-3' (SEQ ID NO: 21)

Probe: 5'-AACTACCGCTGCCAGTTCCACACCAG-3' (SEQ ID NO: 22)
PCR amplicon: 78 bp

TaqMan Reaction and Cycling

Reactions were multiplexed to simultaneously amplify the *E. coli* backbone and polynucleotide of interest. The following qPCR cocktail was prepared: 1.6 µl ddH2O; 5 µl 2× Jump Start™ Taq ReadyMix™ (Sigma, St. Louis, Mo.); 0.2 µl backbone primer and probe mix and 0.2 µl POI primer and probe mix to a final concentration of 300 nM forward primer, 300 nM reverse primer and 100 nM probe. Seven µl of qPCR cocktail was added to each well in a 384-well qPCR plate. Three microliters of different DNA concentrations of fragment DNA or plasmid DNA sample was loaded into the 384-well qPCR plate. The plates were sealed with optically clear heat seal film and the plates spun in a centrifuge. All real-time PCR reactions were performed using an ABI Prism 7900HT Sequence Detection machine (Perkin-Elmer Applied Biosystems, Foster City, Calif.). The thermal cycling conditions included an initial denaturation step at: 95° C. for 5 min followed by 40 cycles of 5 sec at 95° C. and 30 sec at 60° C. for 30 sec.

PCR Efficiency

The PCR efficiency was measured by making standard curves using triplicate serial dilutions of DNA for assay validation. Accordingly, the initial DNA of 20 pg/µl was serially diluted 2-fold (10 pg/µl, 5 pg/µl, 2.5 pg/µl, 1.25 pg/µl, 0.625/µl pg and 0.3125 pg/µl) for the real-time PCR assay according to the standard protocol of Applied Biosystems. The relative standard curve quantification method was previously described (ABI Relative quantification of gene expression. User bulletin No. 2, 1997). Cycle threshold (Ct) is defined as number of cycles at which a selected threshold fluorescence emission ΔRn of the reporter dye is obtained. The cycle threshold is arbitrarily adjusted by examining the semi-log view of the amplification plot. Ct values of serial dilution are plotted against the common logarithm (log 10) concentration of the diluted template. With the slope and after converting the equation, the efficiency of the reaction can be calculated by the formula:

$$E = 10^{\left(\frac{-1}{slope}\right)} - 1 \text{ (Ginzinger D.G., 2002).}$$

$R^2$ coefficient, the correlation coefficient of a standard curve, was obtained by linear regression analysis.

$$R^2 = \left(\frac{\Sigma(x - \bar{x})(y - \bar{y})}{\sqrt{\Sigma(x - \bar{x})^2 \Sigma(y - \bar{y})^2}}\right)^2$$

The equation for the slope of the regression line is:

$$\text{Slope} = \frac{\Sigma(x - \bar{x})(y - \bar{y})}{\Sigma(x - \bar{x})^2}$$

The PCR efficiency should be between 0.9-1.10, the slope between −3.6 and −3.1 and $R^2 \geq 0.98$, where x is the DNA amount (pg/µl) and y is Ct value, $\bar{x}$ is the average of DNA amount in the dilution; $\bar{y}$ is the average of Ct value. For relative quantification, absolute value of the Δslope between the POI and vector backbone should be ≤0.2.

Corn, Sugar Cane Transformation and Genomic DNA Extraction for Real-Time PCR

Corn cultivar AX5707 and sugar cane cultivar L97-128 were transformed by means of particle bombardment. Four discs of seedling leaf tissue from transgenic and wild type plants were ground to a fine powder. Genomic DNA was isolated by using the Wizard® Genomic DNA Isolation System (Promega Corporation, Madison, Wis.) according to the manufacturer's instructions. Each DNA sample was dissolved in 100 µl, 10 mM Tris.Cl (pH8.0). DNA quantification was not necessary. 3 µL of DNA solution was used for real-time PCR reaction.

Data Analysis
Relative Standard Deviations and Confidence Intervals

Confidence limits of detection of the backbone and POI real-time PCR assay was determined using a plasmid DNA (construct ID: 19558) with a series dilution from concentration of 2.5 pg/µL. A 4-fold and 2-fold dilution series of plasmid DNA, from 7.5 pg to $2.38 \times 10^{-6}$ pg DNA per PCR reaction was generated and analyzed in 16 duplicates in the TET (Cat, assay ID 1636) channel and FAM (assay ID 1118) channel of the multiplex PCR assay in order to circumvent sample-to-sample variations and to be able to compare the sensitivity of each single assay.

For the estimation of the amount DNA within the confidence limit of DNA detection, calibration curves were produced by plotting the threshold cycle values (Ct values) versus the logarithm of the DNA amount (pg). The relative standard deviation, RSD, and the 95% relative confidence intervals (95% CI) were calculated by: $RSD=(\sigma/\bar{x}) \times 100$; 95% CI=$(RSD \times t_{df;\alpha})/\sqrt{n}$, where $\bar{x}$ is the mean value, $\sigma$ is the standard deviation, n is the number of replicas at each concentration level, tdf;a is the student factor at a=0.05 and df=n−1 degrees of freedom.

The sample standard deviation is $$\sigma = \sqrt{\Sigma_{i=1}^{N} \frac{(xi-\bar{x})^2}{(n-1)}}$$

The confidence limits at a 95% confidence interval (95% CI) are calculated from the standard deviation using: $\mu = \bar{x} \pm t_{df;\alpha} X \sigma/\sqrt{n}$ For the detection confidence limits of the backbone and POI assays, the RSDs should be less than about 2%.

Example 2

Universal Vector Design for Generating Backbone-Free Transgenic Events Via Particle Bombardment Transformation To linearize circular DNA and remove the E. coli backbone DNA region (bacterial replication DNA region), a plasmid DNA was digested with restriction endonuclease(s) recognizing at least 8 bp DNA sequence to release the polynucleotide-of-interest (POI) fragment from the plasmid vector backbone (see, for example, FIGS. 1 to 5). There are two restriction endonuclease recognition sites (RS1 and RS2) flanking both 5' and 3' ends of the E. coli backbone DNA region. The plasmids can include a nuclease recognition site for a nuclease enzyme, for example, the nuclease enzymes of I-CeuI, PI-PspI, I-SceI, PI-SceI, I PpoI, and/or 8-cutter restriction endonuclease enzymes (AscI, AsiSI, FseI, NotI, PacI, PmeI, SbfI, SfiI, SwaI, SgfI, SrfI, Sse8781I, SdaI). The most commonly used restriction endonucleases are those that recognize 6 bp sequences (six-cutter). Theoretically, there is about one site in a 4.1 kb-fragment on average for a six-cutter restriction endonuclease. The disadvantage of a vector design using 6 cutters is that there is no suitable restriction endonuclease available to release the POI fragment, if the size of vector is large, for instance more than 30 kb. However, there is about one site in a 65.5 kb-fragment on average for a restriction endonuclease that recognizes 8 bp sequences (an 8-cutter). The "rare cutters" (e.g., I PpoI, I-CeuI, PI-PspI, I-SceI, PI-SceI) recognize about a 15-37 bp sequence. Theoretically, there is about one site in a 68719 Mb-fragment (i.e. 1 cut/$4^{18}$ bp) on average for I SceI. Thus, the rare cutters are less likely to cut the POI fragment even in very large vectors because the sites recognized by rare cutters occur less often by chance. Therefore, a further advantage is that the POI will require less engineering to remove restriction sites Most plasmid vector DNA contains the ColE region and an ampicillin resistance gene and further Taq DNA polymerase commonly contains contaminate E. coli DNA or its expression plasmid DNA. Prior to the present invention, there was no assay available that was sensitive enough to detect such an E. coli backbone.

Two primers, a forward primer hybridizing to the junction of one side of the nuclease recognition site (E, coli backbone part) and a reverse primer hybridizing to the junction of the other side of the nuclease recognition site (the polynucleotide of interest part), were designed to amplify either or both of the junctions of the plasmid vector located between the polynucleotide of interest and the plasmid vector backbone (FIG. 5), and to detect the presence or absence of an amplification product. The amplification product comprises at least a portion of the SN1, the restriction nuclease recognition site and at least a portion of SN2, and/or a portion of the SN3, the restriction nuclease recognition site and a portion of SN4. However a backbone assay can be designed to locate in any unique nucleotide sequence if the backbone does not include ColE region and/or an ampicillin resistance gene. An assay for the POI is designed to be located in any unique nucleotide sequence in the POI region. The presence of the amplification product indicates plasmid backbone in the nucleic acid preparation and the absence of the amplification product indicates no vector backbone, and also quantifying the percentage of vector backbone in the nucleic acid preparation.

Amplification Efficiencies of the Target and Backbone

PCR efficiency is important for the accuracy in calculating the amount of vector backbone in a nucleic acid preparation. Constant amplification efficiency in the samples that are compared is one important criterion for reliable comparison between samples. This is especially important when analyzing the relationship between unknown DNA amounts versus a known DNA amount, which is performed in all relative quantification models. To ensure correct calculation of backbone amounts in the backbone free DNA with the POI sequence in real time PCR, the amplification efficiencies should be similar. Both PCR systems were tested with plasmid DNA samples. The DNA samples were serially diluted in 1:2 ratios with 1/10 TE buffer and duplexed assays were run in 16 replicates for each dilution to obtain a standard curve. Two types of vector systems, mini-chromosome vector (19558) and regular vectors (19157, 19158, 19161) have been tested. The four assays, (1) targeting chloramphenicol resistance gene (assay for the backbone, assay ID: 1613); (2) assay ID: 1118 (cCryIAb for POI) for 19558; (3) assay ID: 1072 (POI) and (4) assay ID: 1876 (J1) for 19157, 19158 and 19161 for regular vector were analyzed for the slope, PCR efficiency, $R^2$ (correlation coefficients between Ct value and $\log_{DNA\ concentration}$) and $\Delta$slope.

Figure 6:
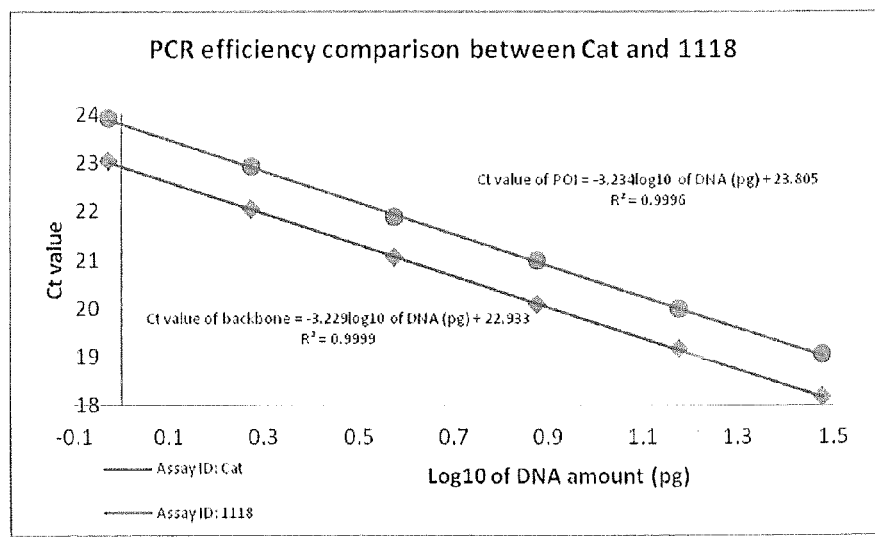
FIG. 6 shows polynucleotide of interest (1118) (○) and backbone (Cat) (◇) assay PCR specific calibration curves for plasmid DNA samples, which were serially diluted in a 1:2 ratio with 1/10TE.
Figure 7:
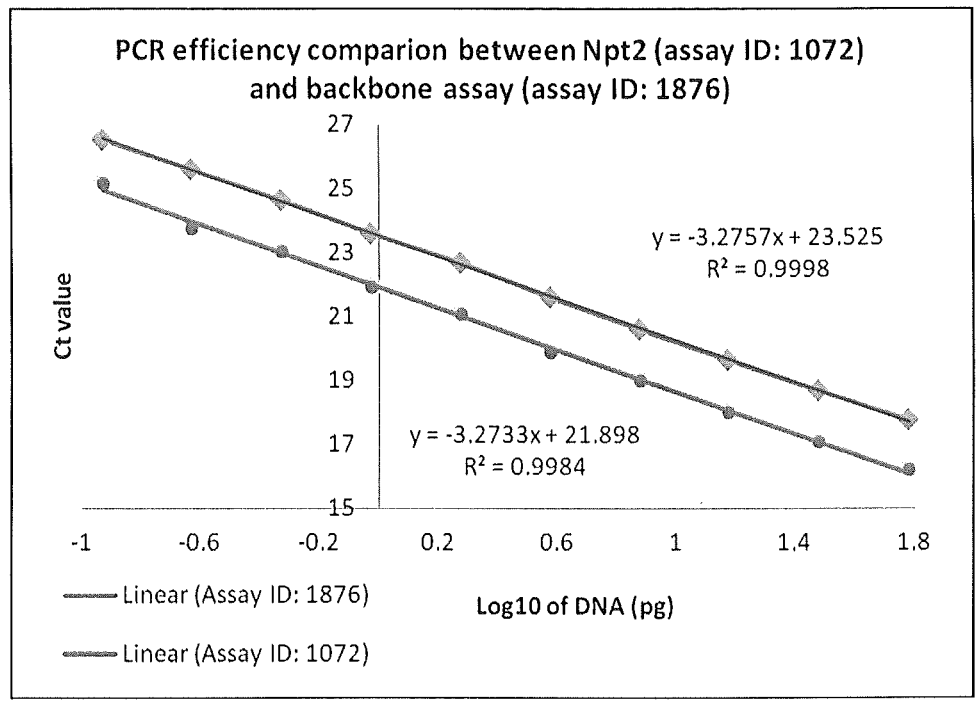
FIG. 7 shows polynucleotide of interest (1072) (○) and backbone (1876) (◇) assay PCR specific calibration curves for plasmid DNA samples, which were serially diluted in a 1:2 ratio with 1/10TE.

Almost identical PCR efficiencies (Table 1) for the backbone assays and POI assays were derived from the slopes of the standard curves (FIG. 6 and FIG. 7). DNA concentration was linear with respect to the amount of backbone present. The results confirm the linear relationship between Ct value and $\log_{DNA\ concentration}$ and indicated that the PCR efficiencies meet the vector backbone calculation requirement, making the Ct value a reliable way to quantify the amount of vector backbone DNA present.

TABLE 1

| | | PCR Efficiency | | | |
| --- | --- | --- | --- | --- | --- |
| Vector type | Assay ID | $-3.587 \leq$ Slope $\leq$ $-3.115$ | $\Delta$Slope $\leq$ 0.2 | PCR efficiency (0.9–1.1) | $R^2 \geq$ 0.98 |
| Mini-Chromosome | Backbone: 1613 | −3.229 | 0.005 | 1.040 | 0.9996 |
| | Fragment assay: 1118 | −3.234 | | 1.038 | 0.9999 |
| Regular vector | Backbone: 1876 | −3.2757 | 0.0024 | 1.0197 | 0.9998 |
| | Fragment assay: 1072 | −3.2733 | | 1.0207 | 0.9984 |

Figure 8:
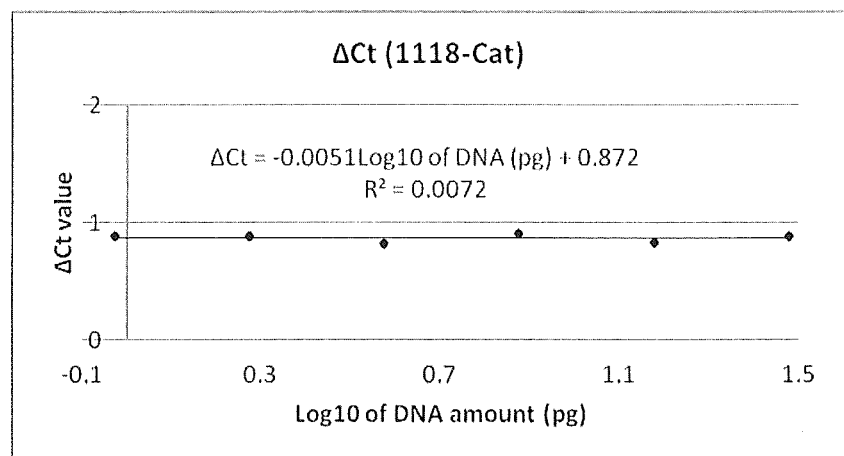
FIG. 8 shows a graphic validation of the $2^{-\Delta\Delta Ct}$ method. The efficiency of amplification of the polynucleotide of interest (Assay 1118) and backbone fragment containing chloramphenicol (Cat assay) was examined using real-time PCR and TaqMan detection. Serial dilutions of plasmid DNA 19558 were amplified by real-time PCR using specific primers. The $\Delta Ct$ ($C_{T,C\text{-}1118}-C_{T,CAT}$) was calculated for each plasmid DNA dilution (Each dilution had 16 duplicates).

The threshold cycle value difference ($\Delta$Ct) between TET Ct and FAM Ct of each reaction was used to normalize the level of total nucleic acid. For this calculation to be valid, as mentioned above the amplification efficiencies of the compared two assays must be approximately equal. A sensitive method for assessing if two amplicons have the same efficiency is to look at how $\Delta C_T$ varies with template dilution. If both reactions have the same efficiency, then $\Delta$Ct ($Ct_{1118}-Ct_{cat}$) does not depend on the dilution series. Thus, plotting $\Delta$Ct versus $\log_{DNA\ concentration}$, the slope should be close to zero. FIG. 8 showed the results of an experiment where a plasmid DNA was diluted over a 64-fold range. The average $C_T$ was calculated for both assay 1118 and Cat and the $\Delta C_T$ ($C_{T,1118}-C_{T,\ Cat}$) was determined. A plot of the log plasmid DNA dilution versus $\Delta C_T$ was made (FIG. 8). As shown in FIG. 8, the slope compare of the line is −0.0051 and the $R^2$ value between them was 0.0072, which is very close to zero, indicating almost no correlation between ($Ct_{FAM}-Ct_{TET}$) and $\log_{DNA\ concentration}$, thus, no or little variation over the series dilution. A similar result was obtained in the regular vector system (data not shown). Thus, using real-time PCR, the assays can accurately determine the amount of vector backbone among samples of varying DNA concentration without prior precise DNA quantification or normalization of each sample, since ($Vt_{FAM}-Ct_{TET}$) is constant regardless of DNA concentration.

Confidence Detection Limits of the Backbone

The limit of detection of the backbone real-time PCR assay was determined using a plasmid DNA (construct ID: 19558). A 4- and 2-fold dilution series of plasmid DNA was generated and analyzed in 16 duplicates in the TET (Cat) channel and FAM (assay #1118) channel of the multiplex PCR assay. To compare the sensitivity of the duplex assay, the 13 plasmid DNA 19558 dilutions were prepared from 7.5 pg (Equivalent to 117265 molecules) to 7.15 ag (0.1 molecule) DNA per PCR reaction. An acceptable detection limit requires meeting the following criteria: (1) the equation for the slope of the regression line should be −3.6 and −3.1; (2) the $R^2$ coefficient, the correlation coefficient of a standard curve should be more than 0.98; (3) the absolute value of the $\Delta$slope between Cat and 1118 should be less than 0.2; and (4) the RSDs of Ct value should be less than 2%.

When the DNA was diluted to 0.114 fg (1.79 molecules), the relationship between log of the amount of 19558 present and the Ct value for the cat assay is described as y=−3.1199 x+21.77 ($R^2$=0.997); the RSD % of the Ct value at the dilution with 0.114 fg DNA was 1.9%; for the 1118 assay, y=−3.2751X+23.206 (R=0.9988); the RSD % of the Ct value at the dilution with 0.114 fg DNA was 3.6%, which did not meet the criteria. However for the POI assay 1118 (target fragment DNA), the DNA is usually set at 7.5 pg, which does not affect the relative quantification. When the DNA was diluted to 0.458 fg (7.12 molecules), the relationship between log of the amount of 19558 present and the Ct value for the cat assay is described as y=−3.2274x+21.713 ($R^2$=0.9997); the RSD % of the Ct value at the dilution with 0.458 fg DNA was 0.95%; for the 1118 assay, y=−3.3198x+23.182 ($R^2$=0.9989); the RSD % of the Ct value at the dilution with 0.458 fg DNA was 1.07%. The result showed that the relationship between log of the amount of 19558 present and the Ct value for the cat and 1118 assays was out of the linear phase. The result also demonstrated that a linear dynamic range was from 7.5 pg to 0.458 fg DNA with the serial dilutions. The detection limit was below 0.458 fg for Cat assay as well as the 1118 assay. The Ct values of 16 replicates of Cat assay when the DNA amount was 0.458 fg were analyzed for the mean value and 95% CI. The result showed that the mean value was 32.414 and 95% confidence interval for actual mean was 32.25 through 32.58. Then 95% CI for DNA amounts were calculated. The calculation indicated that the 95% CI for DNA amounts was 0.429 fg (6.7 molecules) through 0.543 fg (8.5 molecules).

Derivation of Calculation of E. coli Backbone

It has been stated that real-time PCR quantification is based on the description of exponential amplification of PCR is:

$$Xn=Xo\times(1+Ex)^n \qquad 1$$

Where $X_n$ is the number of target molecules at n cycles of the PCR reaction, $X_0$ the initial number of target molecules, n the number of cycles and E the efficiency of the reaction; Ex the efficiency of target amplification (ABI Relative quantization of gene expression. User bulletin No. 2, 1997, www3.appliedbiosystems.com/cms/groups/mcb_support/documents/generaldocuments/cms_040980.pdf).

The formula 1 is applied to derive the following formulas to calculate the amount of vector backbone.

$$\text{Thus, } Xf=Xo\times(1+Ef)^{Ct,f}=Kf \qquad 2$$

Where $X_f$ is the threshold number of target fragment molecules, $C_{t,f}$ is the threshold cycle number at which the amount of amplified target fragment reaches a fixed threshold, $E_f$ the efficiency of target fragment amplification and $K_f$ is a constant.

A similar equation for the backbone reaction is $$Rb = Bo \times (1+Eb)^{Ct,b} = Kb \qquad 3$$

Where $R_b$ is the threshold number of the backbone molecules, Bo the initial number of the backbone molecules, $E_b$ is the efficiency of the backbone fragment amplification, $C_{t,b}$ is the threshold cycle for backbone amplification, and $K_b$ is a constant.

Dividing $R_b$ by $X_f$ gives the amount of vector backbone.

$$\frac{R_b}{x_f} = \frac{B_o \times (1+E_b)^{Ctb}}{x_o \times (1+E_f)^{Ctf}} = \frac{K_b}{K_f} = K \qquad 4$$

As mentioned above, efficiencies of real-time PCR for the different assays are the same, almost equal 1. So, $E_f = E_b = E$
Thus, $$\frac{B_o}{x_o} \times (1+E)^{Ct,b-Ct,f} = K \qquad 5$$

Here, let $\Delta C_{t,q} = C_{t,b} - C_{t,f}$, the difference in threshold cycles for backbone and target fragment. Thus $$\frac{B_0}{X_0} = K \times (1+E)^{-\Delta Ct,q} \qquad 6$$

There are different Ct values for different assays even if there is the same initial number of target molecules. So set a 100% vector backbone as control, i.e. using a plasmid as for the calibrator (cb):

$$\frac{c_b}{c_f} = \frac{c_{bo} \times (1+E_b)^{Ctb\prime}}{c_{fo} \times (1+E_f)^{Ctf\prime}} = \frac{K_{b\prime}}{K_{f\prime\prime}} = K \qquad 7$$

Here, $E_f = E_b = E$; so $\frac{c_{bo}}{c_{fo}} \times (1+E)^{Ct,b\prime - Ct,f\prime} = K \qquad 8$ Let $\Delta C_{t,cb} = C_{t,b\prime} - C_{t,f\prime}$, the difference in threshold cycles for backbone and target from the calibrator.
Thus $$\frac{C_{b0}}{C_{fo}} = K \times (1+E)^{-\Delta Ct,cb} \qquad 9$$

Combined the equation 6 and 9:

$$\frac{\frac{B_o}{X_o}}{\frac{C_{bo}}{C_{fo}}} = \frac{X \times (1+E)^{-\Delta Ct,q}}{X \times (1+E)^{-\Delta Ct,cb}} = (1+E)^{\Delta Ct,cb - \Delta Ct,q}$$

As a calibrator, the initial molecule number of the backbone and target fragment is the same because of using the same amount plasmid DNA. So Cbo=Cfo.

Let $\Delta \Delta Ct = \Delta Ct,q - \Delta Ct,cb$ ($\Delta \Delta Ct > 0$)
Thus, $$\frac{B_0}{X_0} = (1+E)^{-\Delta\Delta Ct}$$

i.e. the vector backbone $$\frac{B_0}{x_0} = (1+E)^{-\Delta\Delta Ct}$$

For amplicons designed to be less than 80 bp and for which the primer and $Mg^{2+}$ concentrations have been properly optimized, our data showed that the efficiency is close to one. Therefore, the amount of vector backbone, normalized to a 100% vector backbone as reference and relative to a calibrator, is given by $$\text{Backbone contamination \%} = \frac{B_0}{X_0} = (2^{-\Delta\Delta Ct}) \times 100\%,$$

(i.e., the percentage vector backbone contamination of the nucleic acid preparation from the formula $(1 \div (2^{[\Delta\Delta CT(Prep-Control)]}) \times 100))$.

Plant Transformation Data Confirmed the Method of Quantifying the E. coli Backbone Contamination To validate this method, the fragments of POI of the plasmids 19157, 19158 and 19161 were transformed into sugarcane cultivar L97-128, and the fragment of POI of the plasmid 19558 was transformed into corn cultivar AX5707 by means of particle bombardment. Four discs of seedling leaf tissue from stable transgenic events and wild type plants of corn and sugarcane were ground to a fine powder. Genomic DNA was isolated by using the Wizard® Genomic DNA Isolation System (Promega Corporation, Madison, Wis.) according to the manufacturer's instructions. Each DNA sample was dissolved in 100 μL 10 mM Tris.Cl (pH8.0). DNA quantification was not necessary. 3 μL of DNA solution was used for real-time PCR reaction. The backbone assay ID 1613 was used to detect the corn transgenic events containing the vector backbone, and the backbone assay ID 1876 was applied to detect the sugarcane transgenic events containing. The backbone contamination data estimated by quantitative Real-time PCR and $T_0$ events in sugarcane and corn are shown in Table 2 and Table 3, below. Using quantitative Real-time PCR, the amount of vector backbone in the POI fragment of 19558 was about 0.63%. In $T_0$ corn transgenic events, 403 transgenic events transformed with 19558 were tested, the result showed that two transgenic events contained the vector backbone, the amount of backbone was about 0.50% (Table 3). Using quantitative Real-time PCR, the amount of backbone in the POI fragments of 19157, 19158 and 19161 were between about 0.10% and about 0.11%, with the average being about 0.11%. In $T_0$ sugarcane transgenic events, 542 transgenic events transformed with 19157 were tested and none were found to contain vector backbone; 658 transgenic events transformed with 19158 were tested and one transgenic event was found to contain vector backbone with the amount of vector backbone being about 0.15%; and finally, 573 transgenic events transformed with 19161 were tested and one transgenic event was found to contain vector backbone with the amount of vector backbone being about 0.17%. Combined with the transformation data, these results indicated that out of 1773 transgenic events, 2 transgenic events contained vector backbone. The backbone contamination was 0.11% (Table 2). We concluded that corn and sugarcane transformation data confirmed the method for determination of vector backbone present in a nucleic acid sample.

TABLE 2

Backbone Contamination Test by quantitative Real-time PCR and T0 Events in corn

| Construct ID | BB Con. % by TaqMan | Event number | BB Con. events | BB con. % in $T_0$ Events |
|---|---|---|---|---|
| 19558 | 0.63 | 403 | 2 | 0.50 |

TABLE 3

Backbone Contamination Test by quantitative Real-time PCR and T0 Events in sugarcane

| Construct ID | BB Con. % by TaqMan | Event number | BB Con. events | BB con. % in $T_0$ Events |
|---|---|---|---|---|
| 19157 | 0.11 | 542 | 0 | 0 |
| 19158 | 0.10 | 658 | 1 | 0.15 |
| 19161 | 0.11 | 573 | 1 | 0.17 |
| Average | 0.11 | 1773 | 2 | 0.11 |

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

That which is claimed is:

1. A method of quantifying the amount of vector backbone in a nucleic acid preparation for use in the transformation of a plant cell, wherein the nucleic acid preparation comprises a polynucleotide of interest (POI), the method comprising:
   a) performing an amplification reaction to amplify a junction located between the POI and a vector backbone, under conditions whereby amplification can occur to produce an amplification product, wherein the junction comprises a recognition site for a nuclease;
   b) quantifying the amount of amplification product in a quantitative amplification assay, wherein the amount of amplification product indicates the amount of vector backbone in said nucleic acid preparation; and
   c) contacting the nucleic acid preparation with a plant cell under conditions favorable for transformation, wherein the cell is subsequently transformed.

2. The method of claim 1, wherein the junction comprises said recognition site linked at one end to a synthetic polynucleotide (SN), and the junction is linked at one end to the POI via the SN and at the other end to the vector backbone via the recognition site and the amplification product comprises the recognition site and at least a portion of the SN.

3. The method of claim 2, wherein the amplifying comprises hybridizing a first oligonucleotide primer to the SN of the junction and hybridizing a second oligonucleotide primer to the vector backbone and the amplification product comprises the recognition site, at least a portion of the SN, and a portion of the vector backbone.

4. The method of claim 1, wherein the junction comprises said recognition site linked at one end to a synthetic polynucleotide SN1 and linked at the other end to a synthetic polynucleotide SN2 and the SN1 of the junction is linked to one of the vector backbone or the POI and the SN2 of the junction is linked to the other of the vector backbone or the POI.

5. The method of claim 4, wherein the amplifying comprises hybridizing a first oligonucleotide primer to the SN1 of the junction and hybridizing a second oligonucleotide primer to the SN2 of the junction and the amplification product comprises the recognition site, at least a portion of SN1 and at least a portion of SN2.

6. The method of claim 4, wherein the synthetic polynucleotide SN1 and the synthetic polynucleotide SN2 are the same or different.

7. The method of claim 5, wherein the synthetic polynucleotide SN1 and the synthetic polynucleotide SN2 are the same or different.

8. The method of claim 1, wherein amplifying comprises amplifying at least about 50 nucleotides of the junction.

9. The method of claim 8 wherein amplifying comprises amplifying about 50 to about 200 nucleotides of the junction.

* * * * *